US009857332B2

(12) United States Patent
Lee et al.

(10) Patent No.: US 9,857,332 B2
(45) Date of Patent: Jan. 2, 2018

(54) SYSTEM FOR MANIPULATING SAMPLES IN LIQUID DROPLETS

(71) Applicant: Tecan Trading AG, Mannedorf (CH)

(72) Inventors: Travis Lee, Brisbane, CA (US); Michael Benjamin Franklin, Bailey, CO (US); Kailiang Wang, Sunnyvale, CA (US); Anne R. Kopf-Sill, Portola Valley, CA (US)

(73) Assignee: TECAN TRADING AG, Mannedorf (CH)

( * ) Notice: Subject to any disclaimer, the term of this patent is extended or adjusted under 35 U.S.C. 154(b) by 780 days.

(21) Appl. No.: 13/737,360

(22) Filed: Jan. 9, 2013

(65) Prior Publication Data
US 2013/0126358 A1 May 23, 2013

Related U.S. Application Data

(63) Continuation-in-part of application No. 13/188,584, filed on Jul. 22, 2011, now Pat. No. 8,470,153.

(51) Int. Cl.
G01N 27/447 (2006.01)
B01L 3/00 (2006.01)
B01L 7/00 (2006.01)

(52) U.S. Cl.
CPC .. G01N 27/44791 (2013.01); B01L 3/502738 (2013.01); B01L 3/502792 (2013.01);
(Continued)

(58) Field of Classification Search
CPC ........ G01N 27/44791; G01N 27/44782; B01L 3/502715; B01L 3/502738;
(Continued)

(56) References Cited

U.S. PATENT DOCUMENTS 5,486,337 A  1/1996  Ohkawa
6,565,727 B1  5/2003  Shenderov
(Continued)

FOREIGN PATENT DOCUMENTS

| CA | WO 2010037763 A1 * | 4/2010 | ........ B01L 3/502784 |
| EP | 1 518 604 | 3/2005 | |
| EP | 1 722 234 | 11/2006 | |
| EP | 2 548 646 | 1/2013 | |
| WO | WO 2007/061943 | 5/2007 | |
| WO | WO 2007/112114 | 10/2007 | |
| WO | WO 2009/052095 | 4/2009 | |

(Continued)

Primary Examiner — Gurpreet Kaur
Assistant Examiner — Maris R Kessel
(74) Attorney, Agent, or Firm — Notaro, Michalos & Zaccaria P.C.

(57) ABSTRACT

A liquid droplet manipulation system has a substrate with at least one electrode array and a central control unit for controlling selection of individual electrodes of the electrode array and for providing the electrodes with individual voltage pulses for manipulating liquid droplets by electrowetting. A working film is placed on top of the electrodes for manipulating samples in liquid droplets with the electrode array. At least one selected individual electrode of the electrode array is configured to be penetrated by light of an optical detection system for the optical inspection or analysis of samples in liquid droplets that are located on the working film. Also disclosed is working film that is to be placed on the electrode array and a cartridge that includes such a working film for manipulating samples in liquid droplets.

22 Claims, 5 Drawing Sheets

(52) U.S. Cl.
CPC ....... *B01L 3/5029* (2013.01); *B01L 3/502715* (2013.01); *B01L 3/523* (2013.01); *B01L 3/527* (2013.01); *B01L 7/52* (2013.01); *B01L 2200/025* (2013.01); *B01L 2200/027* (2013.01); *B01L 2200/04* (2013.01); *B01L 2200/0647* (2013.01); *B01L 2200/141* (2013.01); *B01L 2300/044* (2013.01); *B01L 2300/0672* (2013.01); *B01L 2300/0681* (2013.01); *B01L 2300/089* (2013.01); *B01L 2300/0829* (2013.01); *B01L 2300/0864* (2013.01); *B01L 2300/0867* (2013.01); *B01L 2300/0887* (2013.01); *B01L 2300/161* (2013.01); *B01L 2400/043* (2013.01); *B01L 2400/0427* (2013.01); *B01L 2400/0478* (2013.01); *B01L 2400/0683* (2013.01)

(58) Field of Classification Search
CPC .... B01L 3/502792; B01L 3/523; B01L 3/527; B01L 2300/044; B01L 2300/0672; B01L 2300/0681; B01L 2300/0829; B01L 2300/0864; B01L 2300/0867; B01L 2300/0887; B01L 2300/089; B01L 2300/161; B01L 2220/025; B01L 2200/027; B01L 2200/04
See application file for complete search history.

(56) References Cited

U.S. PATENT DOCUMENTS

| | | | |
|---|---|---|---|
| 8,021,611 B2* | 9/2011 | Roach | G01N 35/04 422/562 |
| 2002/0043463 A1 | 4/2002 | Shenderov | |
| 2006/0254933 A1* | 11/2006 | Adachi | G01N 35/08 205/777 |
| 2007/0217956 A1* | 9/2007 | Pamula | B01F 13/0071 422/400 |
| 2007/0243110 A1* | 10/2007 | Chiou | B01L 3/502792 436/164 |
| 2008/0230386 A1 | 9/2008 | Srinivasan et al. | |
| 2009/0260988 A1* | 10/2009 | Pamula | B01F 11/0071 204/450 |
| 2010/0270156 A1* | 10/2010 | Srinivasan | B01F 13/0071 204/450 |
| 2010/0282609 A1* | 11/2010 | Pollack | B01L 3/5027 204/450 |
| 2013/0126358 A1 | 5/2013 | Lee et al. | |

FOREIGN PATENT DOCUMENTS

| | | |
|---|---|---|
| WO | WO 2009/137415 | 11/2009 |
| WO | WO 2010/069977 | 6/2010 |
| WO | WO 2011/084703 | 7/2011 |

\* cited by examiner

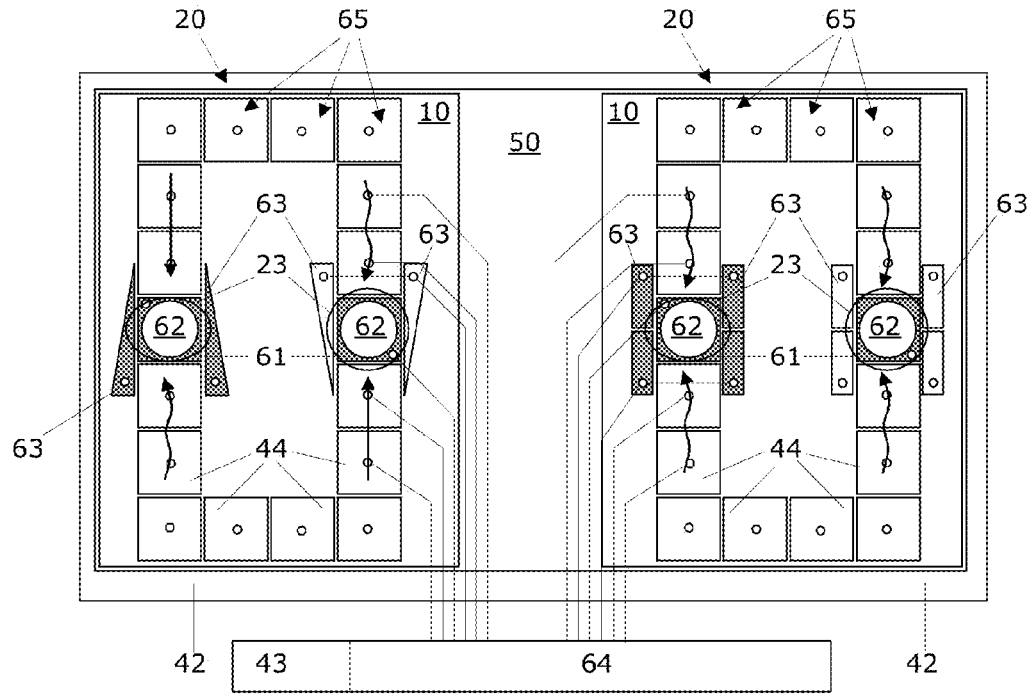

SYSTEM FOR MANIPULATING SAMPLES IN LIQUID DROPLETS

RELATED PATENT APPLICATIONS

The present application is a Continuation in Part Application of the applicant's copending, non-published patent application U.S. Ser. No. 13/188,584 of Jul. 22, 2011. The present application also relates to the non-published applications EP 12 174 408.0 of Jun. 29, 2012; JP 2012-148654 of Jul. 2, 2012; and CN 2012 10254865.1 of Jul. 23, 2012. The entire content of all these non-published applications is herein enclosed by explicit reference for all purposes.

FIELD OF TECHNOLOGY

The present invention relates to a liquid droplet manipulation system and to a cartridge with a polymer film for manipulating samples in liquid droplets thereon. The liquid droplet manipulation system may comprise such a cartridge, an electrode array supported by a substrate, and a central control unit for controlling the selection of individual electrodes and for providing them with individual voltage pulses for manipulating liquid droplets by electrowetting.

The analysis of biological material such as tissue samples or microorganisms, in particular nucleic acids or proteins, is well established in various fields, especially in the field of scientific research, pharmacological screening or forensic sciences, and medical diagnostics. Adequate methods have been developed for different purposes, each method requiring a special set of reaction reagents and devices for the performance of the respective method. However it remains a challenge to adopt existing analysis procedures to the different conditions and requirements present in each field. For example in criminal forensics, a relatively small amount of material to be analyzed is usually available. Additionally, the quality of such material can be rather low, placing additional challenges on the involved personnel. Thus, the procedures need to be specifically adapted to these conditions. On the other hand, for laboratory diagnostic procedures the biological material is usually available in sufficient amounts, but the required methods are to be adopted individually depending on the underlying question to be solved.

For the first steps of the analysis of biological material, there are methods required, which per se are well known in the art. Material of interest is collected e.g. from a crime scene (in criminal forensics) or from a patient (for diagnostic purposes). Such materials can be tissue samples (such as oral mucosa cells, hair follicles) or bodily fluids (such as blood, sputum, etc.). This starting material then requires further processing to make nucleic acids or proteins available for the analysis. Typically, a lysis step is initially applied for these purposes, involving for example the application of heat, a certain enzymatic activity, and/or the application of specific chemicals. The cell lysis is followed by a purification of the nucleic acid or protein of interest from the additional cellular material. In the case where the nucleic acid is to be analyzed, an amplification step might be advisable to increase the sample yield. Nucleic acid amplification is typically achieved by the polymerase chain reaction (PCR). This method allows the amplification of specific, predefined nucleic acid sequences by the use of sequence-specific primer. Depending on the question to be solved, the amplified material might be further analyzed for example by sequencing.

With the progresses in the reliability and simplification of such methods, for example by the use of kits, these methods have become standard procedures in these different fields. Together with an increasing demand for diagnostics based on molecular level, there is an increasing need for the automated processing of relevant samples, starting with an initial biological sample through to the final analysis.

RELATED PRIOR ART

Automated liquid handling systems are generally well known in the art. An example is the Freedom EVO® robotic workstation from the present applicant (Tecan Schweiz AG, Seestrasse 103, CH-8708 Männedorf, Switzerland). This device enables automated liquid handling in a stand-alone instrument or in automated connection with an analytical system. These automated systems typically require larger volumes of liquids (microliter to milliliter) to process. They are also larger systems that are not designed to be portable.

A portable device for lysing and/or purifying biological samples is known from WO 2007/061943. The processing of nucleic acids is performed within a cartridge chamber using electrodes arranged on the two sides, thus processing biological material by electrolysis, electroporation, electro-osmosis, electrical kinetic or resistive heating. The cartridge further comprises sieving matrixes or membranes. By the use of adequate buffers and other reagents, in combination with the application of the electrodes, various reactions can be performed within the chamber, and desired products can be directed for example to collecting membranes. If the sequences of nucleic acids are analyzed, the number of sequences analyzed in parallel is limited to the number of probes. Typically, the number of probes that can be worked on is limited to four different wavelengths that an associated instrument can detect in parallel. The cartridge itself can be placed into an integrated system comprising the required control elements and energy sources. Although this cartridge provides a system to at least partially control the sample processing electronically, intervention of an investigator or of technical lab staff is still required.

Other approaches to deal with the automated processing of biological samples originate from the field of microfluidics. This technical field generally relates to the control and manipulation of liquids in a small volume, usually in the micro- or nanoscale format. Liquid movement in a channel system is known per se as, e.g. being controlled by micro pumps in stationary devices or centripetal forces in rotating labware. In digital microfluidics, a defined voltage is applied to electrodes of an electrode array, so that individual droplets are addressed (electrowetting). For a general overview of the electrowetting method, please see Washizu, IEEE Transactions on Industry Applications, Volume 34, No. 4, 1998, and Pollack et al., Lab chip, 2002, Volume 2, 96-101. Briefly, electrowetting refers to a method to move liquid droplets using arrays of microelectrodes, preferably covered by a hydrophobic layer. By applying a defined voltage to electrodes of the electrode array, a change of the surface tension of the liquid droplet, which is present on the addressed electrodes, is induced. This results in a remarkable change of the contact angle of the droplet on the addressed electrode, hence in a movement of the droplet. For such electrowetting procedures, two principle ways to arrange the electrodes are known: using one single surface with an electrode array for inducing the movement of droplets or adding a second surface that is opposite a similar electrode array and that provides at least one ground electrode. A major advantage of the electrowetting technology is that only a small volume of liquid is required, e.g. a single droplet. Thus, liquid processing can be carried out within considerably shorter time.

Furthermore the control of the liquid movement can be completely under electronic control resulting in automated processing of samples.

A device for liquid droplet manipulation by electrowetting using one single surface with an electrode array (a monoplanar arrangement of electrodes) is known from the U.S. Pat. No. 5,486,337. All electrodes are placed on a surface of a carrier substrate, lowered into the substrate, or covered by a non-wettable surface. A voltage source is connected to the electrodes. The droplet is moved by applying a voltage to subsequent electrodes, thus guiding the movement of the liquid droplet above the electrodes according to the sequence of voltage application to the electrodes.

An electrowetting device for microscale control of liquid droplet movements, using and electrode array with an opposing surface with at least one ground electrode of is known from U.S. Pat. No. 6,565,727 (a biplanar arrangement of electrodes). Each surface of this device may comprise a plurality of electrodes. The drive electrodes of the electrode array are preferably arranged in an interdigitated relationship with each other by projections located at the edges of each single electrode. The two opposing arrays form a gap. The surfaces of the electrode arrays directed towards the gap are preferably covered by an electrically insulating, hydrophobic layer. The liquid droplet is positioned in the gap and moved within a non-polar filler fluid by consecutively applying a plurality of electric fields to a plurality of electrodes positioned on the opposite sites of the gap.

The use of such an electrowetting device for manipulating liquid droplets in the context of the processing of biological samples is known from the US patent application No. 2007/0217956 A1. Here it is suggested to amplify nucleic acids on a printed circuit board for example through thermocycling. The droplets are transported on an array of electrodes by applying a potential between a reference electrode and one or more drive electrodes. The sample is placed into a reservoir on the printed circuit board, and droplets are dispensed on said printed circuit board.

However, none of the above cited devices allow the fully automated processing of nucleic acids starting from collected material up to the final analysis in the small volume scale. An additional disadvantage of the presented devices comes with the nature of such arrangements of electrode arrays, being generally expensive in production, thus being rather non-disposable in use. A continuous reuse of the same device for different biological samples and applications however bears the risk of cross-contaminating the samples of interest, which could lead to false results. Therefore, such devices are not suited for high-throughput assays.

Containers with a polymer film for manipulating samples in liquid droplets thereon are known from WO 2010/069977 A1: A biological sample processing system comprises a container for large volume processing and a flat polymer film with a lower surface and a hydrophobic upper surface. The flat polymer film is kept at a distance to a base side of the container by protrusions. This distance defines at least one gap when the container is positioned on the film. A liquid droplet manipulation instrument comprises at least one electrode array for inducing liquid droplet movements. A substrate supporting the at least one electrode array is also disclosed as well as a control unit for the liquid droplet manipulation instrument. The container and the film are reversibly attached to the liquid droplet manipulation instrument. The system thus enables displacement of at least one liquid droplet from the at least one well through the channel of the container onto the hydrophobic upper surface of the flat polymer film and above the at least one electrode array. The liquid droplet manipulation instrument is accomplished to control a guided movement of said liquid droplet on the hydrophobic upper surface of the flat polymer film by electrowetting and to process there the biological sample.

OBJECTS AND SUMMARY OF THE PRESENT INVENTION

It is an object of the present invention to suggest an alternative liquid droplet manipulation system with an electrode array on which a working film can be positioned, the liquid droplet manipulation system being configured for manipulating samples in liquid droplets and for optically inspecting these samples on the working film placed on the electrode array.

This object is achieved according to a first aspect in that a liquid droplet manipulation system comprising a substrate and an electrode array is suggested, on top of which a working film can be positioned for manipulating samples in liquid droplets thereon. The liquid droplet manipulation system of the current invention comprises a substrate with at least one electrode array and a central control unit for controlling the selection of individual electrodes of the electrode array(s) and for providing the electrodes with individual voltage pulses for manipulating liquid droplets by electrowetting. The liquid droplet manipulation system of the current invention is characterized in that it is configured to receive on top of the electrodes a working film for manipulating samples in liquid droplets with the electrode array(s) when the working film is placed on said electrode array(s), and in that at least one selected individual electrode of the electrode array(s) of the liquid droplet manipulation system is configured to be penetrated by light of an optical detection system for the optical inspection or analysis of samples in liquid droplets that are located on the working film.

Alternatively, the working film may be comprised by a cartridge that is to be placed on the electrode array or the working film may be separately provided on top of the electrode array.

This object is achieved according to a second aspect in that a liquid droplet manipulation system comprising a substrate and an electrode array is suggested, on top of which a cartridge with a working film can be positioned for manipulating samples in liquid droplets with an electrode array of the liquid droplet manipulation system when the working film of the cartridge is placed thereon. The cartridge is characterized in that it comprises:
a) a body that comprises an upper surface, a lower surface, and a number of wells configured to hold therein reagents or samples;
b) a flexibly deformable top structure impermeable to liquids and configured to seal a top side of the wells;
c) a piercable bottom structure impermeable to liquids and configured to seal a bottom side of the wells;
d) a working film located below the lower surface of the body, the working film being impermeable to liquids and comprising a hydrophobic upper surface;
e) a peripheral spacer located below the lower surface of the body and connecting the working film to the body;
f) a gap between the lower surface of the body and the hydrophobic upper surface of the working film, the gap being defined by the peripheral spacer; and g) a number of piercing elements located below piercable bottom structures and configured to pierce the piercable bottom structures for releasing reagents or samples from the wells into the gap.

Additional and inventive features derive from the dependent claims in each case.

Advantages of the Cartridge According to the Present Invention Comprise:

The liquid droplet manipulation system can be utilized to carry out top and/or bottom reading when analyzing the sample in a liquid drop that is manipulated or kept in place on the working film, even when the liquid drop is located in a gap between two surfaces.

Utilizing at least one selected individual electrode of an electrode array of the liquid droplet manipulation system, samples in liquid droplets that are located on the working film over an electrode that is optically transparent or that is an optical via electrode with a through hole can be irradiated by light of an optical detection system for optical inspection or analysis.

The optically transparent electrode or the optical via electrode may be located at any site of an electrode array, e.g. in an electrode path or within a grid-like electrode array of the liquid droplet manipulation system.

The cartridge is designed to physically match for numerous different assays and is therefore generic for a variety of different assays.

The disposable cartridge is designed for single use only and is provided preloaded with prepared treatment liquids and/or reagents in a number and quantity sufficient for the planned assay.

The cartridge is designed for safe intake of specimens such as a buccal swab head, a piece of tissue or blotting paper, liquid samples like blood and the like.

The electrode array is completely separate from the cartridge and can be reused a very large number of times.

The electrode array preferably is of variable design according to the assay that is to be carried out.

The electrode array is not touched by specimen material, samples, or reagents and is thus clean at all times.

With the cartridge and system according to the invention, a single sample can be split into multiple droplets. This enables:
  individual manipulation of single droplets;
  performing separate reactions in each one of these droplets;
  processing each droplet differently and individually; e.g. nucleic acid amplification can be performed and different Single Nucleotide Polymorphism (SNP) can be analyzed in nucleic acid samples in each droplet;
  some of the droplets of a sample can be processes for nucleic acid analysis and other droplets from the same sample can be provided for an immunoassay or reference samples.

BRIEF DESCRIPTION OF THE DRAWINGS

The cartridge and system for manipulating samples in liquid droplets according to the present invention are now explained in more detail with the help of the attached drawings that show preferred, exemplary embodiments of the invention and that are not intended to narrow the scope of the invention. It is shown in:

FIG. 8 detailed 3D views of the specimen intake of a frame-like cartridge according to the third or fourth embodiment, wherein it is shown in:

FIG. 10 a partial top view of two electrode arrays, each one equipped with at least one selected electrode that is configured for the optical inspection or analysis of samples in liquid droplets, wherein FIG. 10A shows two optical via electrodes of a first embodiment with activated or deactivated flanking electrodes, and FIG. 10B shows two optical via electrodes of a second embodiment with activated or deactivated flanking electrodes;

FIG. 11 a partial top view of two electrode arrays, each one equipped with at least one selected electrode that is configured for the optical inspection or analysis of samples in liquid droplets, wherein FIG. 11A shows two optical via electrodes of a third and fourth embodiment without flanking electrodes, and FIG. 11B shows two optically transparent electrodes, one within a grid-like electrode array and one within a single electrode path.

DESCRIPTION OF PREFERRED EMBODIMENTS OF THE INVENTION

Figure 1:
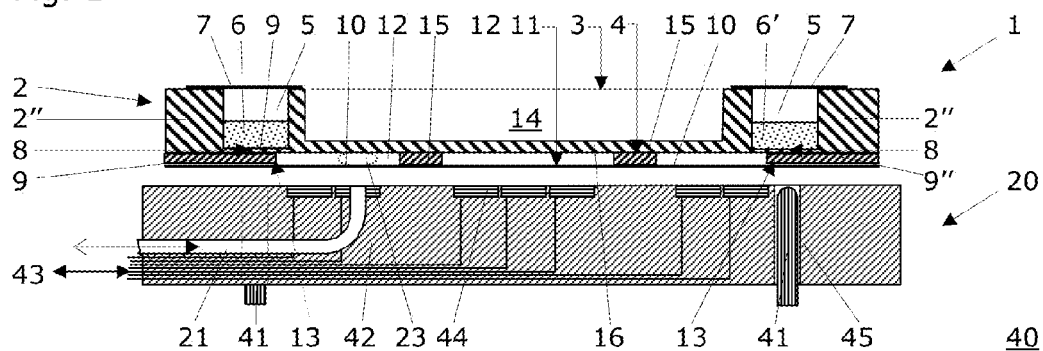
FIG. 1 a vertical cross-section through a frame structured cartridge according to a first embodiment with a central opening closed by a bottom portion, with a number of wells and a working film contacted by a separate peripheral spacer; the cartridge is almost in contact with the electrode array of a system for liquid droplet manipulation.

The FIG. 1 shows a vertical cross-section through a frame structured cartridge 1 according to a first embodiment with a central opening 14 closed by a bottom portion 16, with a number of wells 5 and a working film 10 contacted by a peripheral spacer 9 that is configured as a separate peripheral element 9". The cartridge 1 is almost in contact with the electrode array 20 of a system 40 for liquid droplet manipulation.

This cartridge 1 comprises a working film 10 for manipulating samples in liquid droplets with an electrode array 20 when the working film 10 of the cartridge 1 is placed on said electrode array 20. This cartridge 1 also comprises a body 2, which body 2 preferably comprises an essentially flat lower surface 4. According to the first embodiment, the body 2 is configured as a frame structure 2" with a central opening 14. The body 2 comprises an upper surface 3, a lower surface 4, and a number of wells 5 configured to hold therein reagents 6 or samples 6'. Preferably the material of the body 2 is of an inert plastic material that is impermeable to liquids and that does not take up or interfere with the liquids or samples contained in the wells 5. Preferred materials for injection molding of the body 2 in the form of a frame structure 2" comprise cyclic olefin copolymer (COC), cyclic olefin polymer (COP), polypropylene, polystyrene, polycarbonate, and glass. Preferred production techniques other than injection molding comprise cutting and/or punching of e.g. polytetrafluorethylene or polytetrafluorethen (PTFE).

This cartridge 1 also comprises a flexibly deformable top structure 7 that is impermeable to liquids and that is configured to seal a top side of the wells 5. Preferably an as depicted, the flexibly deformable top structure 7 is configured as a flexible foil that is sealingly attached to the upper surface 3 of the frame structure 2". The flexible foil preferably is made of an elastomeric material, such as a rubber or a thermoplastic elastomer (TPE) membrane and preferably is sealingly attached to the upper surface 3 of the frame structure 2" by welding. Alternatively, the flexibly deformable top structure 7 is configured as a flexible top portion of the body 2 that is integrated in the frame structure 2" (not shown). In this case, the body material preferably is TPE.

This cartridge 1 also comprises a piercable bottom structure 8 that is impermeable to liquids and that is configured to seal a bottom side of the wells 5. Preferably and as depicted, the piercable bottom structure 8 is configured as a piercable bottom portion of the body 2 that is integrated in frame structure 2". In this case, the body material preferably is TPE. Alternatively, the piercable bottom structure 8 is configured as a piercable foil that is sealingly attached to the lower surface 4 of the frame structure 2" (not shown). In this case, the piercable foil preferably is made of an elastomeric material, such as a rubber or a thermoplastic elastomer (TPE) membrane.

This cartridge 1 also comprises a working film 10 that is located below the lower surface 4 of the body 2,2". The working film 10 is impermeable to liquids and comprises a hydrophobic upper surface 11, on which the droplets are to be moved by electrowetting techniques.

According to a first preferred embodiment, the working film 10 is configured as a monolayer of a hydrophobic material:

In the preferred embodiment depicted in FIG. 1, the monolayer of hydrophobic material is also electrically insulating (so that the working film 10 electrically isolates each one of the individual electrodes 44 of the electrode array 20). Thus, the cartridge 1 can directly be placed with its working film 10 on top of the electrode array 20 without any need of an additional dielectric layer. Preferred materials for producing such a preferred dielectric/hydrophobic working film 10 are selected from the group comprising fluorinated ethylene propylene (FEP) such as perfluorethylenepropylene copolymer; perfluoralcoxy polymers and copolymers (PFA); cyclic olefin polymers and copolymers (COP); and polyethylene (PE).

Figure 5:
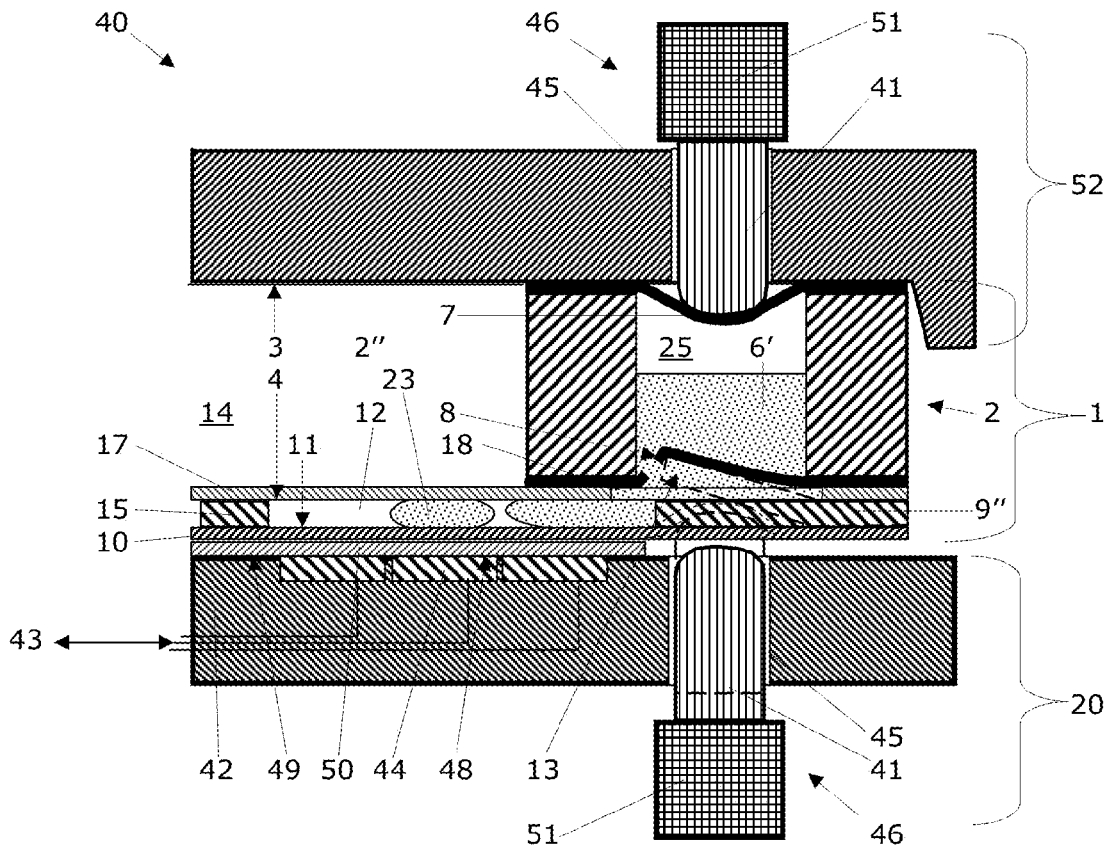
FIG. 5 a vertical cross-section through a frame structured cartridge according to a fourth embodiment with a central opening across the body, with a number of wells and a working film contacted by a separate peripheral spacer; the cartridge is in contact with the electrode array of a system for liquid droplet manipulation; the piercable bottom structure of one well is open and some of its content is pressed into the gap between the working film and a cover layer that is configured as a rigid cover here.

If the monolayer of hydrophobic material however is not electrically insulating (so that working film 10 would cause shortage between the individual electrodes 44 of the electrode array 20) the cartridge 1 must be placed with its working film 10 on top of the electrode array 20 with an additional dielectric layer located between the electrode array 20 and the working film 10 (see e.g. FIG. 5). Such an additional dielectric layer could be attached to the lower surface of the working film 10 or to the upper surface or surface level 48 of the individual electrodes 44 (as in FIG. 5). Alternatively, an additional dielectric layer could be provided as a separate dielectric sheet that is to be positioned on the electrode array 20 before the cartridge 1 is placed thereon with its working film 10 (not shown). A preferred material for producing such a working film 10 of a monolayer of hydrophobic non-dielectric material is for example polytetrafluorethylene or polytetrafluorethen (PTFE).

According to a second preferred embodiment, the working film 10 is configured as a monolayer of electrically non-conductive material of which the upper surface 11 is treated to be hydrophobic. The cartridge 1 can directly be placed with its working film 10 on top of the electrode array 20 without any need of an additional dielectric layer. Such treatment can be coating the monolayer of electrically non-conductive material with silanes (Marcia Almanza-Workman et al. 2002).

According to a third preferred embodiment, the working film 10 is configured as a laminate comprising a lower layer and a hydrophobic upper layer, the lower layer being electrically conductive or non-conductive:

Similar as shown in FIG. 1, the laminate of the working film 10 preferably comprises a dielectric lower layer and a hydrophobic upper layer, so that the working film 10 electrically isolates each one of the individual electrodes 44 of the electrode array 20. Alternatively, a third layer of hydrophobic material can be laminated to the lower side of the dielectric layer so that a sandwich is formed comprising a dielectric layer that is located between two hydrophobic layers. In any case, the cartridge 1 can directly placed with its working film 10 on top of the electrode array 20 without any need of an additional dielectric layer. Preferred material combinations for producing such a preferred laminate working film 10 comprising at least one dielectric and at least one hydrophobic layer are e.g. selected from fluorinated ethylene propylene (FEP) such as perfluorethylenepropylene copolymer for the hydrophobic layer and polyimides (PI) like Kapton® of DuPont for the dielectric layer.

If however the laminate of the working film 10 comprises a lower layer of a non-dielectric material (so that working film 10 would cause shortage between the individual electrodes 44 of the electrode array 20) the cartridge 1 must be placed with its working film 10 on top of the electrode array 20 with an additional dielectric layer located between the electrode array 20 and the working film 10. Such an additional dielectric layer could be attached to the lower surface of the working film 10 or to the upper surface or surface level 48 of the individual electrodes 44 (not shown). Alternatively, an additional dielectric layer could be provided as a separate dielectric sheet that is to be positioned on the electrode array 20 before the cartridge 1 is placed thereon with its working film 10 (see FIGS. 10 and 11).

If there actually is a need to place an additional dielectric layer between the electrode array 20 of a system 40 for liquid droplet manipulation and the working film of the cartridge 1 invention or if there is no such need, it may be preferred to cover the electrode array with an additional dielectric layer just in order to facilitate cleaning of the electrode array 20 of a system 40 for liquid droplet manipulation and for protecting the individual electrodes from being wetted (electrically connected) oxidation or damage.

This cartridge 1 also comprises a peripheral spacer 9 that is located below the lower surface 4 of the body 2,2',2" and that connects the working film 10 to the body 2,2',2". This cartridge 1 also comprises a gap 12 between the lower surface 4 of the body 2,2',2" and the hydrophobic upper surface 11 of the working film 10. This gap 12 is defined by the peripheral spacer 9. Preferably, the peripheral spacer 9 is configured as a peripheral rim 9' that surrounds an area of the gap 12 and that is integrally formed with the body 2 (see FIG. 2). Alternatively and as shown in FIG. 1, the peripheral spacer 9 is configured as a separate peripheral element 9" that surrounds the gap 12 and that is attached to the lower surface 4 of the body 2 that here is configured as a frame structure 2". As depicted, the working film 10 preferably is attached to the separate peripheral element 9" of the frame structure 2".

Preferably, and as large and numerous as necessary, the cartridge 1 comprises intermediate spacers 15 that are located within the area of the gap 12 and that are attached to the lower surface 4 of the body 2 of the frame structure 2". These intermediate spacers preferably have the same height as the separate peripheral element 9" and preferably define the same gap dimension.

This cartridge 1 also comprises a number of piercing elements 13 that are located below piercable bottom structures 8 and that are configured to pierce the piercable bottom structures 8 for releasing reagents or samples 6,6' from the wells 5 into the gap 12. In the embodiment of the cartridge as depicted in FIG. 1, the piercing elements 13 are located within the area of the gap 12 and are integrally formed with the spacer 9 that is configured as a separate ring-like element 9" and that surrounds the gap 12. Preferably, the piercing elements 13 are located below a well 5 or an intake recess and are configured to pierce at least the piercable bottom structure 8 when actuated by an actuating element 41 of a system 40 for liquid droplet manipulation. The actuating elements 41 preferably are guided in their movements by a guiding channel 45.

Preferably, the central opening 14 of the frame structure 2" is configured as a depression in the upper surface 3 of the body 2 leaving a bottom portion 16 of the body 2 that is integrally formed with the frame structure 2" to form the substantially flat lower surface 4 of the body 2. Therefore, it is shown in FIG. 1 that the gap 12 extends between the lower surface 4 of the body 2 and the upper, hydrophobic surface 11 of the working film 10.

Preferably, the substrate 42 comprises at least one optical fiber 21 for bringing light to a droplet 23 (here only indicated in dotted lines) in the gap 12 and/or for guiding light away from a droplet 23 in the gap 12. In FIG. 1, a so called bottom reading optical system is indicated by the optical fiber 21. With this optical system, excitation light (originating from a light source (not shown) can be brought through an individual electrode 44 that is optically transparent (not shown) or that comprises a through hole (shown). The excitation light then penetrates the working film 10 that needs to be optically transparent and enters the droplet 23 with sample material in it. If the sample material comprises a fluorophore, this fluorophore will emit fluorescence that then is detected by the optical bottom reading system and a detector connected to the latter. Accordingly, the bottom reading system in the embodiment shown in FIG. 1 is configured to send excitation light to the sample and to receive and detect fluorescence emitted by the sample. Preferably the optical fiber 21 is integrated into the substrate 42 of the electrode array 20 of the system 40 for the manipulation of droplets. This substrate also comprises electrical lines that link the individual electrodes 44 with a central control unit 43 of the system 40.

Figure 2:
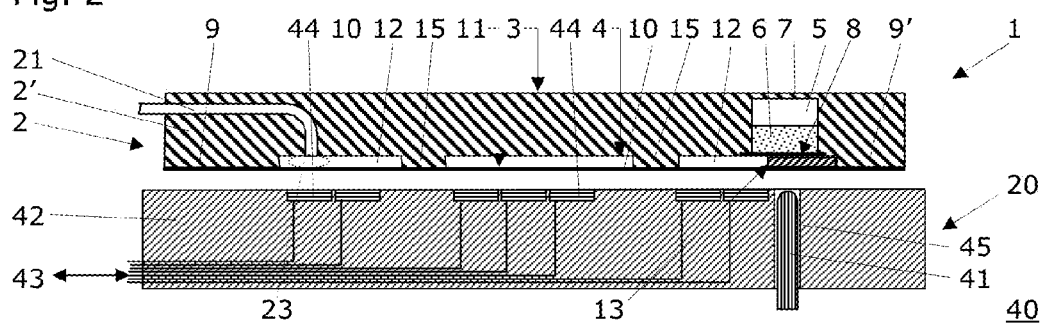
FIG. 2 a vertical cross-section through a plate-like structured cartridge according to a second embodiment with a number of wells and a working film contacted by an integrated peripheral rim; the cartridge is almost in contact with the electrode array of a system for liquid droplet manipulation.

FIG. 2 shows a vertical cross-section through a cartridge 1 with a body 2 that is configured as a plate-like structure 2' according to a second inventive embodiment. This cartridge 1 comprises a number of wells 5 and a working film 10 that is contacted to the body 2 by an integrated peripheral rim 9'. The cartridge 1 is almost in contact with the electrode array 20 of a system 40 for liquid droplet manipulation This cartridge 1 also comprises a working film 10 for manipulating samples in liquid droplets with an electrode array 20 when the working film 10 of the cartridge 1 is placed on said electrode array 20. This cartridge 1 also comprises a body 2, which body 2 preferably comprises an essentially flat lower surface 4. According to the second embodiment, the body 2 is configured as a plate-like structure 2'. The body 2 comprises an upper surface 3, a lower surface 4, and a number of wells 5 configured to hold therein reagents 6 or samples 6'. Like for the frame structure of the first embodiment, the material of the body 2 preferably is of an inert plastic material that is impermeable to liquids and that does not take up or interfere with the liquids or samples contained in the wells 5. The same plastic materials for injection molding of the body 2 as for the frame structure 2" are also preferred for producing the plate-like structure 2' of this embodiment.

This cartridge 1 also comprises a flexibly deformable top structure 7 that is impermeable to liquids and that is configured to seal a top side of the wells 5. Preferably an as depicted in FIG. 2, the flexibly deformable top structure 7 is configured as a flexible top portion of the body 2 that is integrated in the plate-like structure 2'. The material for injection molding of the body 2 and its flexible top portion preferably is TPE. Alternatively, the flexibly deformable top structure 7 is configured as a flexible foil that is sealingly attached to the upper surface 3 of the plate-like structure 2'. The flexible foil preferably is made of an elastomeric material, such as a rubber or a thermoplastic elastomer (TPE) membrane and preferably is sealingly attached to the upper surface 3 of the plate-like structure 2' by welding.

This cartridge 1 also comprises a piercable bottom structure 8 that is impermeable to liquids and that is configured to seal a bottom side of the wells 5. Preferably and as depicted, the piercable bottom structure 8 is configured as a piercable foil that is sealingly attached to the lower surface 4 of the plate-like structure 2'. This piercable foil preferably is made of an elastomeric material, such as a rubber or a thermoplastic elastomer (TPE) membrane. Alternatively, the piercable bottom structure 8 is configured as a piercable bottom portion of the body 2 that is integrated in the plate-like structure 2' (not shown). In this case, the body material preferably is TPE.

This cartridge 1 also comprises a working film 10 that is located below the lower surface 4 of the body 2,2". The working film 10 is impermeable to liquids and comprises a hydrophobic upper surface 11, on which the droplets are to be moved by electrowetting techniques. All embodiments of the working film 10 as well as the additional dielectric layer as described in connection with FIG. 1 are also preferred for the cartridge depicted in FIG. 2.

This cartridge 1 also comprises a peripheral spacer 9 that is located below the lower surface 4 of the body 2,2',2" and that connects the working film 10 to the body 2,2',2". This cartridge 1 also comprises a gap 12 between the lower surface 4 of the body 2,2',2" and the hydrophobic upper surface 11 of the working film 10. This gap 12 is defined by the peripheral spacer 9. Here, the peripheral spacer 9 preferably is configured as a peripheral rim 9' that surrounds an area of the gap 12 and that is integrally formed with the body 2. Alternatively and as shown in FIG. 1, the peripheral spacer 9 is configured as a separate peripheral element 9"' that surrounds the gap 12 and that is attached to the lower surface 4 of the body 2 that here is configured as a frame structure 2". As depicted, the working film 10 preferably is attached to the peripheral rim 9' of the plate-like structure 2'.

Preferably, and as large and numerous as necessary, the cartridge 1 comprises intermediate spacers 15 that are located within the area of the gap 12 and that are integrally formed with the plate-like structure 2'. These intermediate spacers 15 preferably have the same height as the peripheral rim 9' and preferably define the same gap dimension.

This cartridge 1 also comprises a number of piercing elements 13 that are located below piercable bottom structures 8 and that are configured to pierce the piercable bottom structures 8 for releasing reagents or samples 6,6' from the wells 5 into the gap 12. In the embodiment of the cartridge as depicted in FIG. 2, the piercing elements 13 are located within the area of the gap 12 and close to the peripheral rim 9'. The piercing elements 13 here are attached to the peripheral rim 9' and/or to the lower surface 4 of the body 2 of the plate-like structure 2'. Preferably, the piercing elements 13 are located below a well 5 or an intake recess and are configured to pierce at least the piercable bottom structure 8 when actuated by an actuating element 41 of a system 40 for liquid droplet manipulation. The actuating elements 41 preferably are guided in their movements by a guiding channel 45.

Preferably, the cartridge 1 comprises at least one optical fiber 21 for bringing light to a droplet 23 (here only indicated in dotted lines) in the gap 12 and/or for guiding light away from a droplet 23 in the gap 12. In FIG. 2, a so called top reading optical system is indicated by the optical fiber 21. With this optical system, excitation light (originating from a light source (not shown) can be directly brought into the droplet 23 with sample material in it. If the sample material comprises a fluorophore, this fluorophore will emit fluorescence that then is detected by the optical top reading system and a detector connected to the latter. Accordingly, the top reading system in the embodiment shown in FIG. 2 is configured to send excitation light to the sample and to receive and detect fluorescence emitted by the sample. Preferably the optical fiber 21 is integrated into the body 2 of the cartridge 1. As already shown in FIG. 1, the substrate 42 also comprises electrical lines that link the individual electrodes 44 with a central control unit 43 of the system 40.

Figure 3:
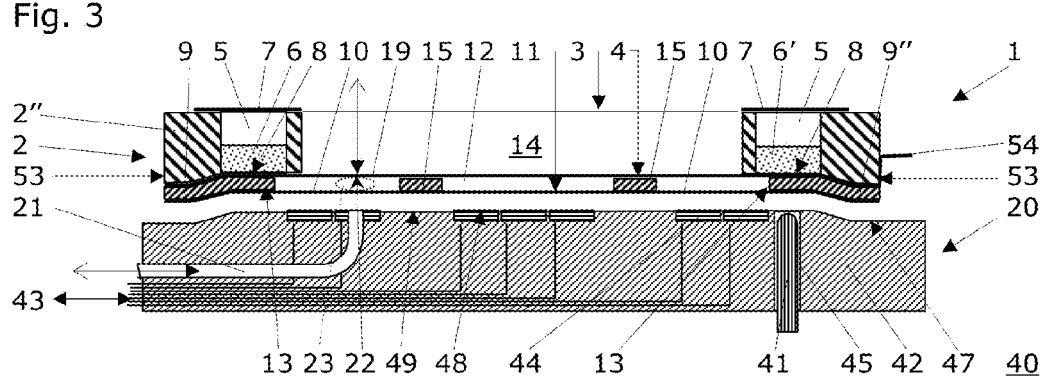
FIG. 3 a vertical cross-section through a frame structured cartridge according to a third embodiment with a central opening across the body, with a number of wells and a working film contacted by a separate peripheral spacer; the cartridge is almost in contact with the electrode array of a system for liquid droplet manipulation.

FIG. 3 shows a vertical cross-section through a frame structured cartridge 1 according to a third embodiment with a central opening 14 across the entire height of the body 2. The cartridge 1 comprises a number of wells 5 and a working film 10 contacted by a spacer 9 that is configured as a separate peripheral element 9"'. The cartridge 1 is almost in contact with the electrode array 20 of a system 40 for liquid droplet manipulation.

This cartridge 1 comprises a working film 10 for manipulating samples in liquid droplets with an electrode array 20 when the working film 10 of the cartridge 1 is placed on said electrode array 20. This cartridge 1 also comprises a body 2, which body 2 preferably comprises an essentially flat lower surface 4. According to the third embodiment, the body 2 is configured as a frame structure 2" with a central opening 14 that extends across the entire height of the body 2. The body 2 comprises an upper surface 3, a lower surface 4, and a number of wells 5 configured to hold therein reagents 6 or samples 6'.

The lower surface 4 of the frame structure 2" of the body 2 is not completely flat: The body 2 comprises an outer part 53 that is extended downwards. Instead of having a completely flat spacer 9 in the form of a separate peripheral element 9"', this embodiment comprises a separate peripheral element 9"' that is downwards bent according to the lower surface of the body 2.

The substrate 42, which is adapted to this special lower surface of the cartridge 1, comprises a surface 49 which is offset to a surface level 48 of the electrodes 44 such that at least a part of the lower surface 4 of the body 2,2',2" or of the spacer 9 of the cartridge 1 to which the working film 10 is attached is movable beyond the surface level 48 of the electrodes 44 for stretching the working film 10 on the electrodes 44.

Preferably the material of the body 2 is of an inert plastic material that is impermeable to liquids and that does not take up or interfere with the liquids or samples contained in the wells 5. The same plastic materials for injection molding of the body 2 as for the frame structure 2" in FIG. 1 are also preferred for producing the frame structure 2" of this embodiment.

This cartridge 1 also comprises a flexibly deformable top structure 7 that is impermeable to liquids and that is configured to seal a top side of the wells 5. Preferably an as depicted, the flexibly deformable top structure 7 is configured as a flexible foil that corresponds to the flexible foil in FIG. 1.

This cartridge 1 also comprises a piercable bottom structure 8 that is impermeable to liquids and that is configured to seal a bottom side of the wells 5. Preferably and as depicted, the piercable bottom structure 8 is configured as a piercable cover layer 19. This cover layer 19 is configured as a piercable foil that is sealingly attached to the lower surface 4 of the frame structure 2" in a way that the cover layer 19 closes the gap 12 on a side opposite to the working film 10. Preferably, the lower surface of the cover layer 19 is essentially flush with the lower surface 4 of the frame structure 2".

Preferably the cover layer 19 is electrically conductive and is hydrophobic at least on a surface directed to the gap 12. The cover layer may also be chosen such that the material of the cover layer 19 is from an electrically conductive and hydrophobic material, e.g. PTFE. In this case of an electrically conductive cover layer 19, a cartridge 1 is preferred that comprises an electrical ground connection 54 which is connected to the cover layer 19 and which is attachable to a ground potential source of the system 40 for liquid droplet manipulation.

This cartridge 1 also comprises a working film 10 that is located below the lower surface 4 of the body 2,2". The working film 10 is impermeable to liquids and comprises a hydrophobic upper surface 11, on which the droplets are to be moved by electrowetting techniques. All embodiments of the working film 10 as well as the additional dielectric layer as described in connection with FIGS. 1 and 2 are also preferred for the cartridge depicted in FIG. 3.

This cartridge 1 also comprises a peripheral spacer 9 that is located below the lower surface 4 of the body 2,2',2" and that connects the working film 10 to the cover layer 19 and to the body 2,2',2". This cartridge 1 also comprises a gap 12 between the cover layer 19 and the hydrophobic upper surface 11 of the working film 10. This gap 12 is defined by the peripheral spacer 9. Here, the peripheral spacer 9 is configured as a separate peripheral element 9" that surrounds an area of the gap 12 (compare with FIG. 1). As depicted, the working film 10 preferably is attached to the separate peripheral element 9" of the frame structure 2".

Preferably, and as large and numerous as necessary, the cartridge 1 comprises intermediate spacers 15 that are located within the area of the gap 12 and that are attached to the lower surface of the cover layer 19 and/or to the hydrophobic upper surface 11 of the working film 10. These intermediate spacers 15 preferably have the same height as the separate peripheral element 9" and preferably define the same gap dimension.

This cartridge 1 also comprises a number of piercing elements 13 that are located below wells 5 or below an intake recess and that are configured to pierce the cover layer 19 for releasing reagents or samples 6,6' from the wells 5 or the intake recess into the gap 12. In the embodiment of the cartridge as depicted in FIG. 3, the piercing elements 13 are located similarly than shown in FIG. 1. Preferably, the piercing elements 13 are actuated by an actuating element 41 of a system 40 for liquid droplet manipulation. The actuating elements 41 preferably are guided in their movements by a guiding channel 45.

Here, the central opening 14 of the frame structure 2" is configured as a through hole from the upper surface 3 to the lower surface 4 of the body 2 e 2". Here, the cover layer 19 forms the substantially flat lower surface 4 of the body 2.

Preferably, the substrate 42 comprises at least one optical fiber 21 for bringing light to a droplet 23 (here only indicated in dotted lines) in the gap 12 and/or for guiding light away from a droplet 23 in the gap 12. In addition or alternately, it may be preferred to provide a window 22 in the cover layer 19 at a place that is opposite the gap 12 and in register with the entrance/exit opening of the optical fiber 21. In consequence, bottom reading (compare with FIG. 1) and/or top reading (compare with FIG. 2) is enabled by the third embodiment of FIG. 3. Preferably the optical fiber 21 is integrated into the substrate 42 of the electrode array 20 of the system 40 for the manipulation of droplets. This substrate also comprises electrical lines that electrically connect the individual electrodes 44 with a central control unit 43 of the system 40.

Figure 4:
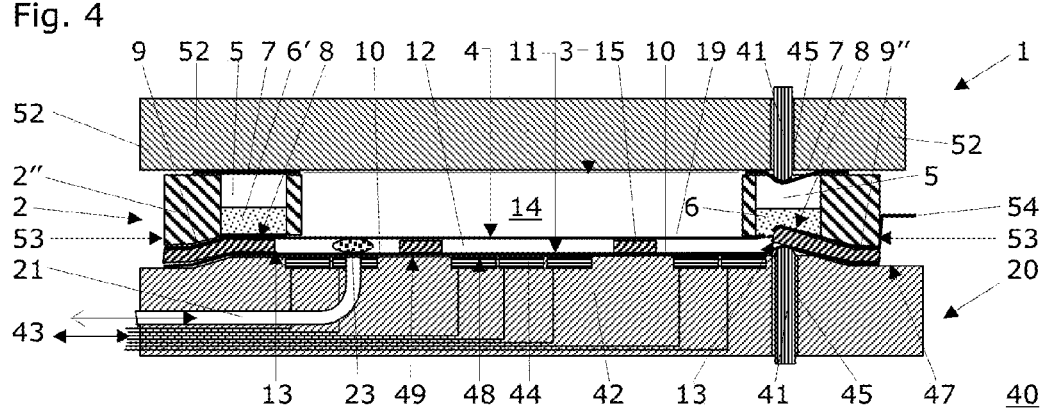
FIG. 4 a vertical cross-section through the frame structured cartridge according to the third embodiment of FIG. 3; the cartridge is in contact with the electrode array of a system for liquid droplet manipulation, the piercable bottom structure of one well is open and some of its content is pressed into the gap between the working film and a cover layer.

FIG. 4 shows a vertical cross-section through the frame structured cartridge 1 according to the third embodiment of FIG. 3. The cartridge 1 is in contact with the electrode array 20 of a system 40 for liquid droplet manipulation. The piercable bottom structure in the form of a cover layer 19 is opened for one well 5 and some of its content is pressed into the gap 12 between the working film 10 and the cover layer 19.

Like the substrate 42 in FIG. 3, the substrate 42 here comprises an abutment surface 47 which is offset to a surface level 48 of the electrodes 44 such that a separate peripheral element 9" of the cartridge 1 to which the working film 10 is attached, is movable beyond the surface level 48 of the electrodes 44 for additionally stretching the working film 10 on the electrodes 44.

In this preferred embodiment of a system 40 for liquid droplet manipulation, a clamping mechanism 52 presses the cartridge 1 and its working film 10 onto the surface 48 of the electrodes 44 and onto the surface 49 of the substrate 42.

FIG. 5 shows a vertical cross-section through a frame structured cartridge 1 according to a fourth embodiment with a central opening 14 across the body 2, with a number of wells 5 and a working film 10 contacted by a separate peripheral spacer element 9". The cartridge 1 is in contact with the electrode array 20 of a system 40 for liquid droplet manipulation. The piercable bottom structure 8 of one well (the intake recess 25) is opened and some of its content is pressed into the gap 12 between the working film 10 and a cover layer 19 that is configured as a rigid cover 17 here. The material for this rigid cover preferably is Mylar®, a transparent, flexible polyester foil on the basis of polyethylene terephthalat from DuPont. The rigid cover 17 may be coated on its underside with a layer of indium tin oxide (ITO) in order to provide the rigid cover 17 with an electrically conductive layer that can be connected to a ground potential source of the system 40 for liquid droplet manipulation. This FIG. 5 also depicts a system 40 for liquid droplet manipulation that comprises a cartridge 1 and an electrode array 20.

This cartridge 1 comprises a working film 10 for manipulating samples in liquid droplets 23 with an electrode array 20 when the working film 10 of the cartridge 1 is placed on said electrode array 20. This cartridge 1 also comprises a body 2, which body 2 preferably comprises an essentially flat lower surface 4, which is built by rigid cover 17 here. According to the fourth embodiment, the body 2 is configured as a frame structure 2" with a central opening 14 that extends across the entire height of the body 2. The body 2 comprises an upper surface 3, a lower surface 4, and a number of wells 5 and intake recesses 25 configured to hold therein reagents 6 or samples 6'.

Preferably the material of the body 2 is of an inert plastic material that is impermeable to liquids and that does not take up or interfere with the liquids or samples contained in the wells 5. The same plastic materials for injection molding of the body 2 as for the frame structure 2" in FIGS. 1, 3, and 4 are also preferred for producing the frame structure 2" of this embodiment.

This cartridge 1 also comprises a flexibly deformable top structure 7 that is impermeable to liquids and that is configured to seal a top side of the wells 5. Preferably an as depicted, the flexibly deformable top structure 7 is configured as a flexible foil that corresponds to the flexible foil in the FIGS. 1, 3, and 4.

This cartridge 1 also comprises a piercable bottom structure 8 that is impermeable to liquids and that is configured to seal a bottom side of the wells 5 and intake recesses 25. Preferably and as depicted, the piercable bottom structure 8 is configured as a piercable foil that is sealingly attached (e.g. by welding) to the lower surface 4 of the body 2. This piercable foil preferably is made of an elastomeric material, such as a rubber or a thermoplastic elastomer (TPE) membrane. Alternatively, the piercable bottom structure 8 is configured as a piercable bottom portion of the body 2 that is integrated in the plate-like structure 2' (compare FIG. 1). In that case, the body material preferably is TPE.

In order to enable the piercing elements 13 for piercing the piercable bottom structure 8, the rigid cover 17 comprises cover holes 18, through which the piercing elements 13 easily reach the piercable foil. Preferably, the working film 10 is flexible so that no leaking out of liquids from the gap 12 has to be expected. All embodiments of the working film 10 as well as the additional dielectric layer as described in connection with the FIGS. 1 to 4 are also preferred for the cartridge depicted in FIG. 5.

The substrate 42, which is adapted to this flat lower surface of the cartridge 1, comprises a surface 49 which is flush with a surface level 48 of the electrodes 44 such that the working film 10 is stretched on the electrodes 44. An electrically insulating film, layer or cover 50 is applied to the surface 48 of the electrodes 44 and to the surface 49 of the substrate 42. This electrically insulating film, layer or cover 50 preferably is a dielectric layer that irremovably coats the electrodes 44 and substrate 42 of the system 40 for liquid droplet manipulation. It is however also preferred to provide an additional dielectric layer as a removable electrically insulating layer or cover 50 that can be replaced when needed.

The spacers 9,15 and piercing elements 13 of this cartridge 1 correspond with the spacers 9,15 and piercing elements 13 in FIG. 1 and define a gap 12 between the rigid cover 17 and the hydrophobic upper surface 11 of the working film 10. Preferably, the piercing elements 13 are actuated by an actuating element 41 of a system 40 for liquid droplet manipulation. The actuating elements 41 preferably are guided in their movements by a guiding channel 45. As depicted, the rigid cover 17 has essentially the same extension as the frame structure 2" and comprises a number of holes 18 located below the wells 5. The holes 18 have a size and shape sufficient to allow bended piercing elements 13 to abut and pierce a respective piercable bottom structure 8 of a well 5.

In an alternative embodiment, the cartridge 1 comprises a rigid cover 17 and a cover layer 19 (the latter replacing the piercable foil as a piercable bottom structure 8). The rigid cover 17 and the cover layer 19 are attached to the frame structure 2" in a way that the rigid cover 17 closes the gap 12 on a side opposite to the working film 10, a lower surface of the rigid cover 17 being essentially flush with the lower surface 4 of the frame structure 2". The cover layer 19 (not shown in FIG. 5) preferably is placed between the rigid cover 17 and the lower surface 4 of the body 2.

Preferably, the actuating elements 41 are configured as plungers that are slidingly movable in guiding channels 45 and that are agitated by an agitation mechanism 46. It also preferred that the agitation mechanism 46 for agitating the actuating elements 41 is configured as one of a wax pump bladder, a solenoid driven or clamping mechanism driven lever 51. It is further preferred that the agitation mechanism 46 for agitating the actuating elements 41 is configured as a clamping mechanism driven lever 51 and that the clamping mechanism 52 being hand driven and configured to press the body 2,2',2" of a cartridge 1 onto the substrate 42 and electrode array 20 of the system 40 for liquid droplet manipulation. Alternately, the clamping mechanism 52 is motor driven.

Figure 6:
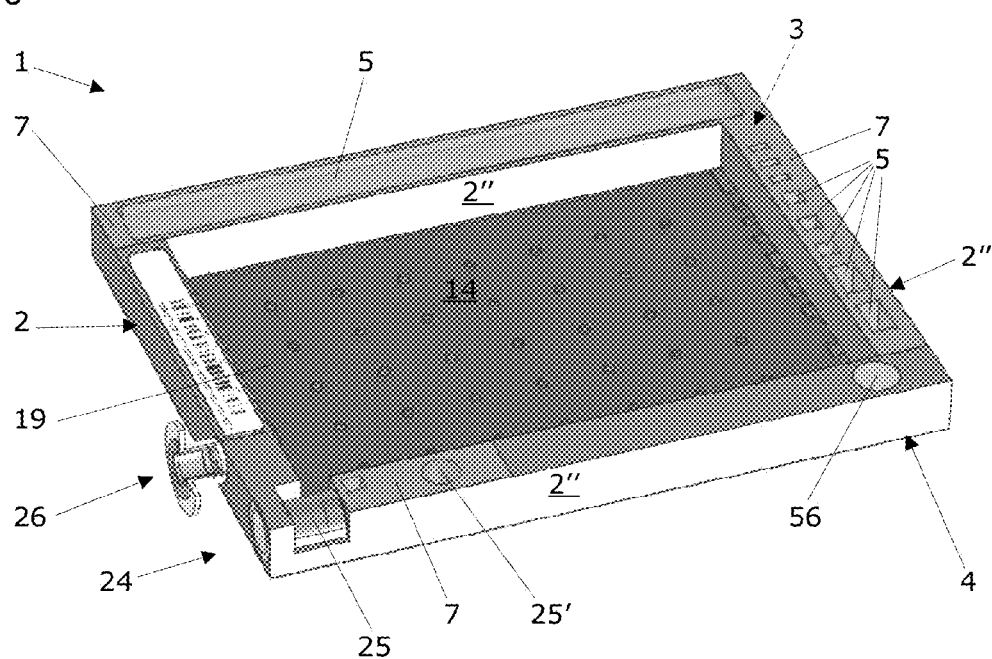
FIG. 6 a 3D top view of a frame-like cartridge according to the third or fourth embodiment with an intake device in a passive position.

The FIG. 6 shows a 3D top view of a frame-like cartridge 1 according to the third or fourth embodiment with an intake device 26 in a passive position. The body 2,2" of the cartridge 1 preferably comprises a specimen intake 24 that comprises an intake recess 25 and an intake device 26, the intake device 26 being at least partially positionable in an active position in the intake recess 25. This specimen intake 24 is configured to introduce a buccal swab head 55 or other solid material comprising a sample to investigate.

The FIG. 6 also shows in the cross bar of the body 2 on the right side of the cartridge a number of wells 5 of different size for pre-depositing reagents and other liquids like wash fluids etc. In the longitudinal bar on the rear of the body 2 is shown a very long well 5, which is configured to take up pre-deposited oil. The oil can be used for filling the gap 12 prior to enter sample drops into the gap 12. Complete filling of the gap 12 with an oil that is not miscible with the samples that normally are contained in a hydrous droplet and that is inert (e.g. silicon oil) is optional. As can be seen from FIG. 6, the size of the wells 5 can be chosen according to the actual need for carrying out particular assays. A flexibly deformable top structure 7 that is configured as foil impermeable to liquids seals the top side of the wells 5. The flexible foil is sealingly attached to the upper surface 3 of the frame structure 2" by laser welding for example.

In the longitudinal bar on the front of the body 2 is shown an alternative intake recess 25' for introducing a sample of body fluid (like blood, saliva, etc.). This alternative intake recess 25' preferably is sealed on its top side by a foil that is impermeable to liquids, but that is also piercable with a needle of a medical syringe and that is flexible for being pushed by a piston-like actuating element for bringing the sample into the gap 12 of the cartridge 1 after the piercable bottom structure 8 has been pierced from the bottom side of the cartridge 1 with a piercing element 13. The material for the foil that seals the top side of the alternative intake recess 25' preferably is rubber.

In the right front corner of the cartridge, a frit 56 that is located in a channel which reaches down to the lower surface 4 of the body 2 and that preferably is combined with a semi-permeable membrane (not shown) is depicted. This frit 56 and the channel serves as a vent for the gap 12 as soon as a piercable bottom structure 8 that sealingly closes the bottom of the channel has been pierced from the bottom side of the cartridge 1 with a piercing element 13.

A large number of intermediate spacers 15 can be seen through the optically transparent rigid cover 17 or cover layer 19. Although all intermediate spacers 15 drawn here are of equal size and round shape, and although these intermediate spacers 15 are distributed over the gap 12 at equal distances, the shape, size and distribution of these intermediate spacers 15 can be chosen as needed, if the intended electrowetting movements of the droplets 23 are not compromised.

Figure 7:
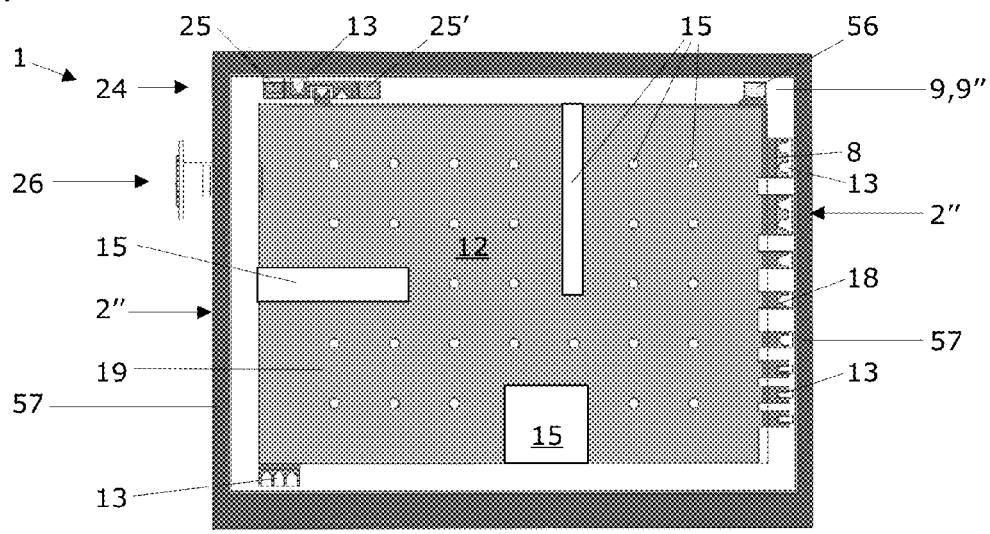
FIG. 7 a bottom view of a frame-like cartridge according to the third or fourth embodiment of FIG. 6 with an intake device in a passive position.

The FIG. 7 shows a bottom view of a frame-like cartridge 1 according to the third or fourth embodiment of FIG. 6 with an intake device 26 in a passive position. The working film 10 has been removed here so that the spacer 9 configured as a peripheral element 9" is visible. Deviating from the cross sections shown in the FIGS. 4 and 5, where the peripheral element 9" extends to the outer borders of the cartridge 1, the peripheral element 9" here is bordered by a downward extension 57 of the body 2. This downward extension 57 of the body 2 in combination with the lower surface of the working film 10 (that is attached to the peripheral element 9") preferably provides the entire cartridge with a flat lower surface. Alternately, the downward extension 57 of the body 2 is flush with the peripheral element 9" and the working film 10 is attached to the working film 10 and as well to the downward extension 57 of the body 2.

As being parts of the peripheral element 9'', many piercing elements 13 can be seen here. Depending from the size of the well 5 above, the size and number of the piercing elements 13 can vary: i.e. for the oil containing well, three piercing elements 13 are depicted (see lower left); for the two largest wells that contain reagents, two piercing elements 13 are depicted (see upper right); and for the smaller wells containing reagents, only one piercing element 13 are depicted (see lower right). The piercing element 13 that is configured to pierce the piercable bottom structure 8 below the intake recess 25 is shown on the left side of the top bar of the body 2. The shown number, size and shape of these piercing elements 13 is only exemplary here and can vary according to actual needs.

As already noted with respect to FIG. 6, the shape, size and distribution of the intermediate spacers 15 can be chosen as needed, if the intended electrowetting movements of the droplets 23 are not compromised. Here are three exemplary intermediate spacers 15 shown that clearly deviate from the ones of FIG. 6.

The FIG. 8 shows detailed 3D views of the specimen intake 24 of a frame-like cartridge 1 according to the third or fourth embodiment.

Figure 8A:
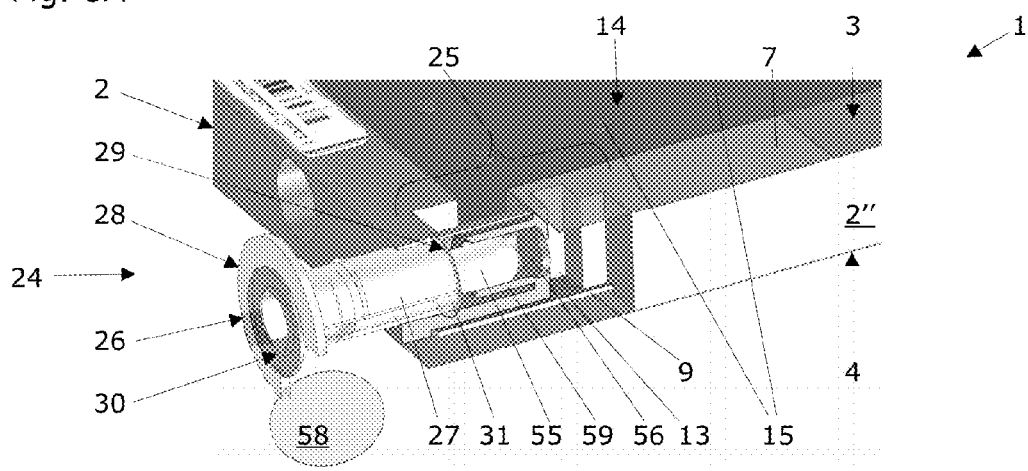
FIG. 8A a semi cross-section of the specimen intake of the frame-like cartridge with a partially inserted intake device in the active position.

FIG. 8A shows a semi cross-section of the specimen intake 24 of the frame-like cartridge with a partially inserted intake device 26 in the active position. The intake device 26 preferably comprises a cylinder tube 27 with a first end 28 and with a second end 29, a plunger 30 that is insertable on the first tube end 28 and that is movable in the cylinder tube 27, and a sealing foil 31 that sealingly closes the second end 29 of the cylinder tube 27. In the space inside the cylinder tube 27 and between the plunger 30 and the sealing foil 31, a pre-deposit of lysis buffer is provided. A frit 56 is also visible. This frit 56 separates the part of the intake recess 25 (the outer chamber) in which the sample carrier, such as a buccal swab head 55, is placed for lysis of cellular material and the part of the intake recess 25 (the inner chamber) where the lysate is pressed into after the lysis. The intake device 26 obviously has been moved from the passive position (see FIGS. 6 and 7) to the active position, where the intake recess 25 of the cartridge 1 is located. A flexibly deformable top structure 7 that is configured as a foil and that is impermeable to liquids seals the top side of intake recess 25. The flexible foil is sealingly attached to the upper surface 3 of the frame structure 2'' by laser welding for example.

Figure 8B:
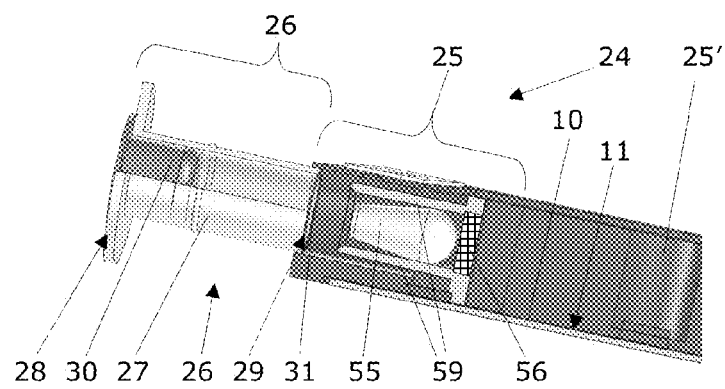
FIG. 8B a semi cross-section of the specimen intake of the frame-like cartridge and of the partially inserted intake device in the active position.

FIG. 8B shows a semi cross-section of the specimen intake 24 of the frame-like cartridge 1 and of the partially inserted intake device 26 in the active position. The situation depicted here is the following:

1. A sample was taken with a buccal swab and the specimen (the buccal swab head 55 with the adhering sample) was introduced into the outer chamber of the intake recess 25 after peeling off a seal 58 that prevents the intake recess 25 from contamination before use (see FIG. 8A).
2. The intake device 26 is now pushed into the intake recess 25. The outer circumference of the cylinder tube 27 is sealing gliding in the cylinder-like outer chamber of the intake recess 25.

The next steps of introducing a sample into the gap 12 of the cartridge 1 will be:

3. The intake device 26 is pushed further into the intake recess 25 until a piercing structure 59 in the outer chamber of the intake recess 25 is piercing the sealing foil 31 that sealingly closes the second end 29 of the cylinder tube 27.
4. The lysis buffer originally contained in the cylinder tube 27 is entering the outer chamber of the intake recess 25 and the intake device 26 is pushed further into the intake recess 25 in order to push out air through the frit 56 between the outer and the inner chamber of the intake recess 25.
5. Lysis of cellular material that adheres to the swab head 55 is performed. During lysis, the temperature preferably is enhanced in the intake recess 25. A heater in the substrate 42 of the system 40 for manipulating droplets (or alternately in the cartridge 1) is preferably used for raising the temperature inside the intake recess 25 to the required values.
6. After lysis, the cylinder tube 27 of the intake device 26 is completely pushed into the outer chamber of the intake recess 25. When doing this, a large portion of the lysate is pressed through the frit 56 and enters the inner chamber of the intake recess 25.
7. If required, the gap 12 of the cartridge is first filled with oil. The piercable bottom structure 8 below the inner chamber of the intake recess 25 then is pierced by pushing a piercing element 13 against the piercable bottom structure 8 with the help of a plunger 41.
8. The flexibly deformable top structure 7 that sealingly closes the top of the inner chamber of the intake recess 25 is pushed inwards with the help of a plunger 41 and by reducing the internal volume of the inner chamber of the intake recess 25 some of the lysate is release to the gap 12.

Figure 9:
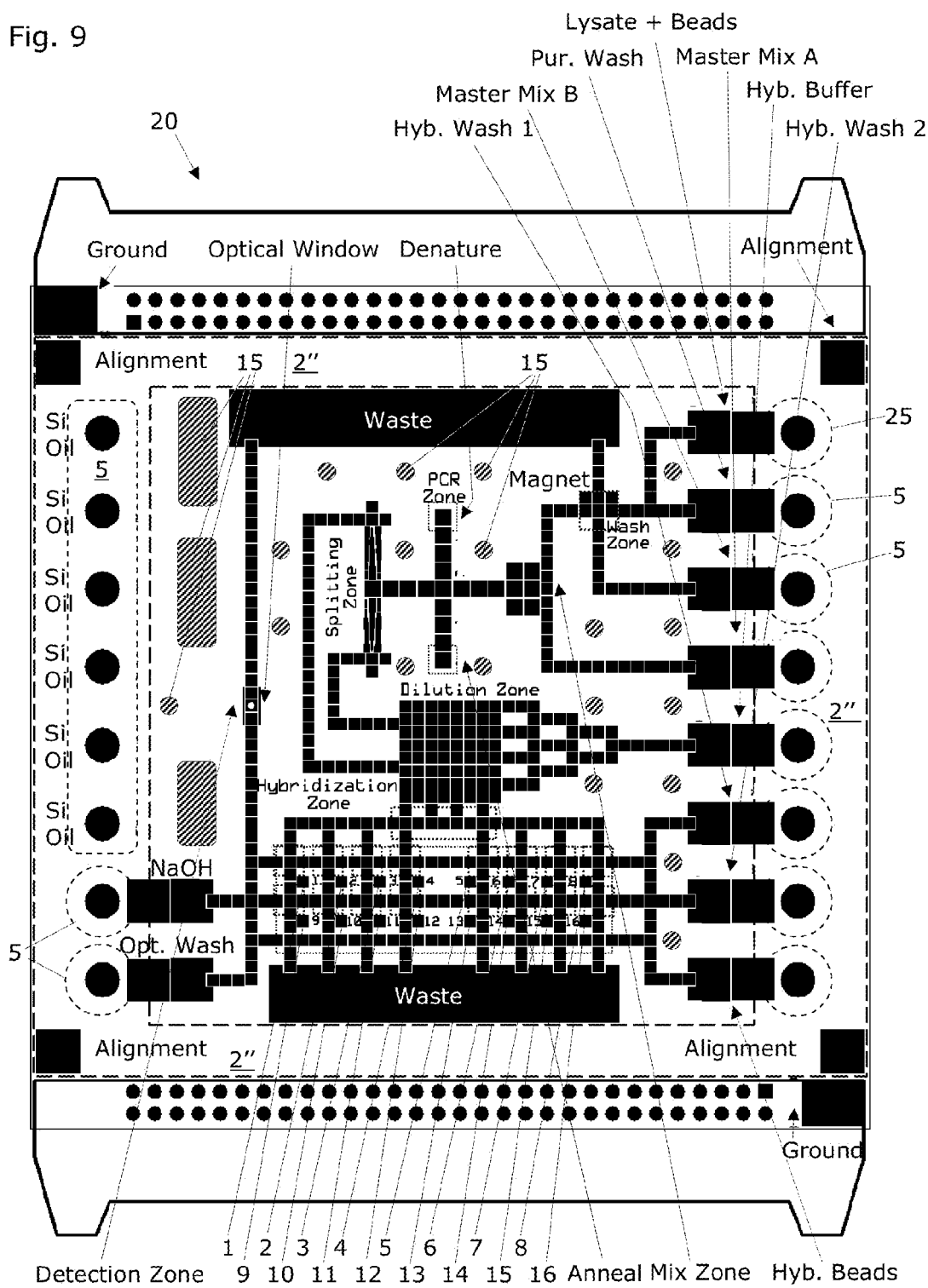
FIG. 9 a top view of an electrode layout of a system for liquid droplet manipulation that is configured for receiving a frame-like cartridge according to the third or fourth embodiment, the layout being particularly configured to match for lysis of cellular material, for extraction and PCR amplification of DNA fragments, for hybridization experiments for genotyping, and for optical detection.

The FIG. 9 shows a top view of an electrode layout or printed circuit board (PCB) of a system 40 for liquid droplet manipulation. This particular electrode array 20 of the system 40 is configured for receiving a frame-like cartridge 1 according to the third or fourth embodiment. Accordingly, the shape of the cartridge 1 with its central opening 14 is indicated in longer dashed lines here. The shape of the wells 5 and intake recess 25 is indicated in shorter dashed lines.

This electrode array 20 is particularly configured to match for the lysis of cellular material, for the extraction and PCR amplification of DNA fragments, for the hybridization experiments for genotyping, and for the optical detection. Four alignment marks in the corners of the electrode array facilitate alignment of the array.

Starting on the left (if required), the entire gap 12 is flooded with silicon (Si) oil. Then (see top right), from the intake recess 25 lysate (with or without beads) is entering the gap 12. Directly at the entrance to the gap 12, where the piercable bottom structure 8 of the corresponding well 5 is pierced, preferably is located a first large electrode that is accompanied by a second large electrode. The second large electrode in each case has a cut out, where the first of a row of individual electrodes 44 is placed.

These two large electrodes mark the area, where a portion of the liquid from the respective well 5 or intake recess 25 is deposited after piercing the piercable bottom structure 8 from below and pressing the flexible deformable top structure 7 from the top. From this portion of liquid, single small droplets of a typical volume of 0.1 to 5 µl are separated. The wells adjacent to the intake recess 25 (from top to bottom of the FIG. 9) are assigned to pure wash liquid, master mix B, master mix A, hybridization buffer, hybridization wash solution 1, hybridization wash solution 2, and beads for hybridization.

A droplet of lysate and of pure wash liquid are moved by electrowetting to the wash zone where these droplets are mixed and washed and the magnetic beads and attached non-important sample parts are moved to a first waste zone, which is provided by a very large electrode. At the wash zone and at the adjacent mix zone, master mix portions A and/or B can be added to the sample droplet. Then, a droplet is moved to the zone for polymerase chain reaction (PCR) where the nucleic acids contained in the sample droplet are amplified according to techniques known per se. The PCR zone comprises at least two heater zones with a different temperature (e.g. 35° C. and 95° C.) for annealing and separating the strands of the nucleic acids.

Following PCR, a single ample drop with amplified nucleic acids is split into two smaller droplets at a splitting zone that preferably is characterized by the particular shape and arrangement of electrodes as depicted. In the central dilution zone, both of these two sample droplets are individually diluted with hybridization buffer and up to eight identical droplets are produced from each one of these two split sample droplets.

At the hybridization spots 1-4 and 9-12 or 5-8 and 13-16, the twice eight sample droplets are subjected to hybridization according to techniques known per se. Following hybridization, the added, non-hybridized material is thoroughly washed away and discarded in a nearby second waste zone (which again is provided by a very large electrode).

Each one of the sixteen sample droplets is then individually moved (with electrowetting again) to a detection zone, where (using bottom reading, top reading, or a mixture or combination of both) the hybridized samples are optically analyzed.

Following analysis of the samples in the sample droplets that are still in the gap 12 of the cartridge 1, the samples are discarded to the first waste zone and the "electrowetting path" provided by a large row of individual electrodes 44 is washed and cleaned a sodium hydroxide solution (NaOH) and optionally with a special wash solution.

When all the experiments and measurements are completed, the cartridge 1 (together with the samples and the waste in it) is safely discarded so that nobody of the laboratory personnel is endangered by its contents. Then, the next cartridge 1 is pressed onto the electrode array 20 and the next experiments can be performed.

In the FIG. 9 (see on top and on the bottom of the Figure), a large number of contact points are seen. Individual electric lines contact each electrode with one of these contact points. In addition, heaters located in the substrate 42 of the system 40 are also connected to some of these contact points. All contact points are connected with the central control unit 43 which controls all necessary activations of e.g. heaters, plungers 41 etc. and of all electrical potentials of the electrodes that are required. On each side of the electrode array is also provided a separate contact point for contacting with ground potential source of the central control unit 43.

Preferably, the system 40 for liquid droplet manipulation comprises a substrate 42 with an electrode array 20 and a central control unit 43 for controlling the selection of individual electrodes 44 of the electrode array 43 and for providing the electrodes 44 with individual voltage pulses for manipulating liquid droplets 23 by electrowetting. The preferred system 40 is configured to receive on top of the electrodes 44 the working film 10 of a cartridge 1 according to the present invention.

The system 40 can be a stand alone and immobile unit, on which a number of operators is working with cartridges 1 that they bring along. The system 40 thus may comprise a number of substrates 42 and a number of electrode arrays 20, so that a number of cartridges 1 can be worked on simultaneously and/or parallel. The number of substrates 42, electrode arrays 20, and cartridges 1 may be 1 or any number between e.g. 1 and 100 or even more; this number e.g. being limited by the working capacity of the central control unit 43. Alternatively, the system 40 can be can be implemented as a hand held which only comprises and is able to work with a single cartridge 1. Every person of skill will understand that intermediate solutions that are situated in-between the two extremes just mentioned will also operate and work within the gist of the present invention.

The expressions "electrode array", "electrode layout", and "printed circuit board (PCB)" are utilized in this patent application as synonyms. Any combination of the features of the different embodiments of the cartridge 1 disclosed in this patent application that appear reasonable to a person of skill are comprised by the gist and scope of the present invention. Even if they are not particularly described in each case, the reference numbers refer to similar elements of the cartridge 1 and system 40 of the present invention.

The FIG. 10 shows a partial top view of two electrode arrays 20, each one being equipped with two selected individual electrodes 44 that are configured as optical via electrodes 61 for the optical inspection or analysis of samples in liquid droplets 23. FIG. 10A shows two optical via electrodes 61 of a first embodiment with activated or deactivated flanking electrodes 63 in a triangular shape. FIG. 10B shows two optical via electrodes 61 of a second embodiment with activated or deactivated flanking electrodes 63 in a rectangular shape. This liquid droplet manipulation system 40 comprises a substrate 42 with two electrode arrays 20 and with a central control unit 43 that is configured for controlling the selection of individual electrodes 44 of the electrode arrays 20 and for providing these electrodes 44 with individual voltage pulses for manipulating liquid droplets 23 by electrowetting.

According to the present invention, the liquid droplet manipulation system 40 is configured to receive on top of the electrodes 44 a working film 10 (here, two individual working films 10 are shown) for manipulating samples in liquid droplets 23 with the electrode arrays 20 when the working film 10 is placed on at least one of said electrode arrays 20. Alternatively, a working film 10 can have a smaller size that only covers a part of an electrode array 20 or a larger size that covers more than one electrode arrays (depending on the actual assay to be carried out). Further according to the present invention, at least one selected individual electrode 44 of the electrode arrays 20 of the liquid droplet manipulation system 40 is configured to be penetrated by light of an optical detection system for the optical inspection or analysis of samples in liquid droplets 23 that are located on the working film 10. Here in each case, the two selected individual electrodes 44 are configured as optical via electrodes 61, each of which comprising a through hole 62.

An electrically insulating film or cover 50 is placed over the electrode arrays 20 in order to provide electrical insulation between the individual electrodes 44 of the electrode path 65 and between the liquid droplets 23 and the electrodes 44. In this case, the working film is removable (peelable) from the insulating film or cover 50 and will be replaced each time a new experiment or assay is to be carried out. Of course, only for simplicity of demonstration, the electrode path 65 shown is a closed loop; the electrode path 65 can be much more complex (e.g. comprising branches, crossings, arrays, reservoirs, and waste sinks) as exemplary can be seen in FIG. 9.

In FIG. 10A, the optical via electrodes 61 are accompanied by flanking electrodes 63 in the form of two similar orientated triangles, situated laterally to the optical via electrodes 61 and also connected to the electrode selection unit 64 of the central control unit 43 of the liquid droplet manipulation system 40 like all individual electrodes 44 and like the optical via electrodes 61. For simplicity of the drawing, only a few of the electrical connections between the electrode selection unit 64 and the individual electrodes 44 present on (or in) the substrate 42 are drawn. FIG. 10A shows two optical via electrodes 61 of a first embodiment with activated or deactivated flanking electrodes 63. The activated electrodes are shown in grey, the inactivated electrodes or electrodes kept at ground potential are shown in white. This liquid droplet manipulation system 40 comprises a substrate 42 with two electrode arrays 20 and with a central control unit 43 that is configured for controlling the selection of individual electrodes 44 of the electrode arrays 20 and for providing these electrodes 44 with individual voltage pulses for manipulating liquid droplets 23 by electrowetting.

When testing this layout of the electrode array 20 as shown in FIG. 10A, it has been recognized that the droplets 23 may move in a somewhat "wavy" fashion if they approach the optical via electrodes 61 towards the site where the triangular flanking electrodes 63 exhibit their broad border (see wavy arrows). In contrast, straight movement of the liquid droplets 23 was observed when they approach the optical via electrodes 61 towards the site where the triangular flanking electrodes 63 exhibit their tip border (see straight arrows). Preferably, both flanking electrodes 63 of a single optical via electrode 61 are electrically connected with each other so that they always exhibit the same electrical potential (see right side). It was also observed that when placed on an optical via electrode 61 of this first embodiment, a liquid droplet 23 exhibits an elliptic shape if the flanking electrodes 63 are activated (see on the left), and that a liquid droplet 23 exhibits an circular shape if the flanking electrodes 63 are deactivated (see on the right). Drifting off of the droplet 23 from the site of the through hole 62 of the optical via electrode 61 was not observed when the flanking electrodes 63 were deactivated.

In FIG. 10B, the optical via electrodes 61 are accompanied by flanking electrodes 63 in the form of four similar orientated rectangles, pairwise situated laterally to the optical via electrodes 61 and also connected to the electrode selection unit 64 of the central control unit 43 of the liquid droplet manipulation system 40 like all individual electrodes 44 and like the optical via electrodes 61. For simplicity of the drawing, only a few of the electrical connections between the electrode selection unit 64 and the electrodes 44 present on (or in) the substrate 42 are drawn. The activated electrodes are shown in grey, the inactivated electrodes or electrodes kept at ground potential are shown in white.

When testing this layout of the electrode array 20 as shown in FIG. 10B, it has been recognized that the droplets 23 may move in a somewhat "wavy" fashion if they approach the optical via electrodes 61 (see wavy arrows).

The FIG. 11 shows a partial top view of two electrode arrays 20, each one being equipped with two selected individual electrodes 44 that are configured for the optical inspection or analysis of samples in liquid droplets 23. FIG. 11A shows two optical via electrodes 61 of a third and fourth embodiment without flanking electrodes. FIG. 11B shows two optically transparent electrodes 60, one located within a grid-like electrode array 26 and one located within a single electrode path 65.

This liquid droplet manipulation system 40 comprises a substrate 42 with two electrode arrays 20 and with a central control unit 43 that is configured for controlling the selection of individual electrodes 44 of the electrode arrays 20 and for providing these electrodes 44 with individual voltage pulses for manipulating liquid droplets 23 by electrowetting.

According to the present invention, the liquid droplet manipulation system 40 is configured to receive on top of the electrodes 44 a working film 10 (here, two individual working films 10 are shown) for manipulating samples in liquid droplets 23 with the electrode arrays 20 when the working film 10 is placed on at least one of said electrode arrays 20. Alternatively, a working film 10 can have a smaller size that only covers a part of an electrode array 20 or a larger size that covers more than one electrode arrays (depending on the actual assay to be carried out). Further according to the present invention, at least one selected individual electrode 44 of the electrode arrays 20 of the liquid droplet manipulation system 40 is configured to be penetrated by light of an optical detection system for the optical inspection or analysis of samples in liquid droplets 23 that are located on the working film 10. In FIG. 11A, the two selected individual electrodes 44 are configured as optical via electrodes 61, each of which comprising a through hole 62, and each of which having no flanking electrodes 63 nearby. In FIG. 11B, the two selected individual electrodes 44 are configured as optically transparent electrodes 60, each of which having no flanking electrodes 63 nearby.

An electrically insulating film or cover 50 is placed over the electrode arrays 20 in order to provide electrical insulation between the individual electrodes 44 of the electrode path 65 or of the grid-like electrode array 66 and between the liquid droplets 23 and the electrodes 44. In this case and preferably, the working film is removable (peelable) from the insulating film or cover 50 and will be replaced each time a new experiment or assay is to be carried out. Of course, only for simplicity of demonstration, the electrode path 65 shown is a closed loop and the grid-like electrode array 66 is rather small. The electrode path 65 can be much more complex (e.g. comprising branches, crossings, arrays, reservoirs, and waste sinks) and the grid-like electrode array 66 much larger. Combinations of electrode paths 65 and grid-like electrode arrays 66 are also possible, as exemplary can be seen in FIG. 9.

All individual electrodes 44 are operatively connected with the electrode selection unit 64 of the central control unit 43 of the liquid droplet manipulation system 40. For simplicity of the drawing, only a few of the electrical connections between the electrode selection unit 64 and the individual electrodes 44 present on (or in) the substrate 42 are drawn. The activated electrodes are shown in grey, the inactivated electrodes or electrodes kept at ground potential are shown in white.

On the left side of FIG. 11A, the optical via electrode 61 of the third embodiment is divided into two partial electrodes, each of which comprising a part of the through hole 62. These two partial electrodes can be individually connected to the electrode selection unit 64 so that they can be individually activated or deactivated; this has the advantage of shifting a liquid droplet 23 more towards the adjacent electrode 44 of the electrode path 65, when only one of these partial electrodes is activated. In consequence, transportation of the liquid droplet 23 is facilitated. In a simpler alternative, these two partial electrodes of the optical via electrode 61 are electrically connected to each other so that only one connection exists with the electrode selection unit 64, consequently both so partial electrodes are simultaneously activated or deactivated.

On the right side of FIG. 11A, the optical via electrode 61 of the fourth embodiment comprises a though hole 62 and lateral wings that at last partially surround an adjacent electrode of the electrode path 65. Activating this optical via electrode 61 of the fourth embodiment (including its wings) causes shifting of a liquid droplet 23 more towards the adjacent electrode 44 of the electrode path 65 (in the upward direction in FIG. 11A), which facilitates transportation of the liquid droplet 23. In the opposite transportation direction, activating this optical via electrode 61 of the fourth embodiment (including its wings) facilitates moving of a liquid droplet 23 onto the optical via electrode 61 and its though hole 62.

When testing this layout of the electrode array 20 as shown in FIG. 11A, it has been recognized that the droplets 23 always move straight when they approach the optical via electrodes 61 no matter from which side (see straight arrows). It was also observed that when placed on an optical via electrode 61 of this third or fourth embodiment, a liquid droplet 23 exhibits a slightly elliptic shape.

On the left side of FIG. 11B, a single optically transparent electrode 60 situated within a grid-like electrode array 66 is activated; thus, a single droplet 23 can be analyzed with the optics of the liquid droplet manipulation system 40. Instead of only one single optically transparent electrode 60, an array of optically transparent electrodes 60 could be located within a grid-like electrode array 66 and all simultaneously activated; thus, a larger aggregate of single droplets 23 can be analyzed.

On the right side of FIG. 11B, a single optically transparent electrode 60 situated within an electrode path 65 is activated; thus, a single droplet 23 can be analyzed with the optics of the liquid droplet manipulation system 40.

When testing this layout of the electrode array 20 as shown in FIG. 11B, it has been recognized that the droplets 23 always move in a perfectly straight way towards the optically transparent electrodes 60 (see straight arrows in the FIG. 11B), no matter from which direction the liquid droplets arrive to or depart from the optically transparent electrodes 60. It was also observed that when placed on an optically transparent electrode 60, a liquid droplet 23 always exhibits a circular shape.

For all testing of the optically transparent electrodes 60 and the optical via electrodes 61, the following parameters were chosen:
Root Mean Square Voltage: 220 V and 180 V
Pulse Frequency: 3 Hz
Droplet Volume: 2 μl
Sample: Dyed Tris buffer
Gap height: 0.5 mm
Electrode size:
Diameter of the through hole 62: 1.0 mm (preferred minimum) to 1.1 mm (preferred) to 1.25 mm (preferred maximum).

The diameter of the through hole 62 strongly depends on the actual size and shape of the respective optical via electrode 61 and is preferably as large as possible with the provision that the optical via electrode 61 still affects a liquid droplet 23 as required when being provided with individual voltage pulses for manipulating liquid droplets 23 by electrowetting. It is reasonable to relate the respective areas of an optical via electrode 61 and its through hole 62 to each other. An optical via electrode 61 with square shape of 1.5×1.5 mm has an area of 2.25 mm$^2$ and a circular through hole 62 of 1 mm diameter has an area of 0.79 mm$^2$; of 1.1 mm diameter has an area of 0.95 mm$^2$, and of 1.25 mm diameter has an area of 1.23 mm$^2$. Relating these areas provides for the following area ratios (optical via electrode 61: through hole 62): 2.25:0.79; 2.25:0.95, and 2.25:1.23 or approximately to 2.8; 2.4; and 1.8. With other words, the area ratio (optical via electrode 61: through hole 62) preferably is from 1.8 to 2.8; most preferably is 2.4.

With respect to the optical via electrodes 61, the fastest response time has been observed on the types of the fourth embodiment (see FIG. 11A, right side). However (as already reported), the droplet 23 will always be sitting on the hydrophobic surface 11 of the working film 10 with a slightly elliptical profile. The second fastest response time has been observed on the types of the third embodiment (see FIG. 11A, left side); the droplet 23 will always be sitting on the hydrophobic surface 11 of the working film 10 with a slightly elliptical profile as well.

It has also been observed that liquid droplets can be moved in a straight manner on a hydrophobic upper surface 11 of a working film 10 that is placed on an electrode array 20 as depicted in the FIGS. 10A and 10B, if the flanking electrodes 63 are turned off. This is in good agreement with the observation with respect to embodiment as shown in FIG. 11B, where it has been recognized that the droplets 23 always move in a perfectly straight way towards and from the optically transparent electrodes 60 that are devoid of flanking electrodes 63.

Preferably, the spot (see white spots in the FIG. 11) of electrically connecting the optically transparent electrode(s) 60 with the electrode selection unit 64 of the liquid droplet manipulation system 40 is located near the border (e.g. near a corner) of the optically transparent electrode(s) 60 in order to leave as much as possible area for optically investigating the sample in a droplet 23 placed over the optically transparent electrode(s) 60. It is also preferred that the spot (see white spots in the FIGS. 10 and 11) of electrically connecting the optical via electrodes 61 with the electrode selection unit 64 of the liquid droplet manipulation system 40 is located near the border (e.g. near a corner) of the optical via electrodes 61 in order to leave as much as possible area for the through hole 62 and thus for optically investigating the sample in a droplet 23 placed over the optical via electrodes 61. The spot (see white spots in the FIGS. 10 and 11) of electrically connecting the individual electrodes 44 with the electrode selection unit 64 of the liquid droplet manipulation system 40 may be selected as convenient (e.g. in the center of the individual electrodes 44 as shown).

As already pointed out, the optics of the liquid droplet manipulation system 40 may comprise an optical bottom reading system and a detector connected to the latter. Moreover, the optics of the liquid droplet manipulation system 40 may comprise an optical top reading system and a detector connected to the latter. In addition, the optics of the liquid droplet manipulation system 40 may comprise a combined optical bottom and top reading system and one or more related detectors. These optical systems can be adapted to the inspection or analysis of single droplets 23, but also to the inspection or analysis of larger aggregates of single droplets 23. All optical systems can comprise lenses for influencing the light for exciting or inspection of the samples and also lenses for influencing the light penetrating or emitted by the samples in the liquid droplets 23. With respect to the optics, the arrangement of optical fibers 21 as depicted in the FIGS. 1 to 4 are preferred.

Preferably, all electrodes 44,60,61,63, whether they are part of an electrode path 65 or of a grid-like electrode array, are located flush with the surface 49 of the substrate 42 or embedded (situated inside, but close to the surface 49) in the substrate 42. All electrical connections preferably are embedded into the substrate 42, at the border of which they can be assembled in a multi-pin plug (e.g. in the case of FIG. 10) for connecting the electrode array(s) 20 with the electrode selection unit 64 of the liquid droplet manipulation system 40. The substrate 42 with the electrode array(s) 20 thus can be attached to the central control unit 43 (see FIG. 10). Alternatively, the central control unit 43 can be at least partially integrated into the substrate (see FIG. 11).

Preferably, the optically transparent electrodes 60 are produced from ITO (Indium tin oxide), which is a solid solution of indium(III) oxide ($In_2O_3$) and tin(IV) oxide ($SnO_2$), typically 90% $In_2O_3$, 10% $SnO_2$ by weight. The ITO material is transparent and colorless in thin layers (only in the infrared region of the spectrum, ITO it acts as a metal-like mirror). Indium tin oxide is one of the most widely used transparent conducting oxides because of its two chief properties, its electrical conductivity and optical transparency, as well as the ease with which it can be deposited as a thin film. As with all transparent conducting films, a compromise must be made between conductivity and transparency, since increasing the thickness and increasing the concentration of charge carriers will increase the material's conductivity, but decrease its transparency. Thin films of indium tin oxide are most commonly deposited on surfaces by electron beam evaporation, physical vapor deposition, or a range of sputter deposition techniques. In consequence, the ITO material may be deposited on a PCB with similar techniques as used for the deposition of the material for the individual electrodes 44.

Preferably, in connection with the embodiments of optically transparent electrodes 60,61 as shown in the FIGS. 10 and 11 and in the extent of implementing optical top and/or bottom reading, the electrically insulating film 50, the working film 10, the cover layer 19, the rigid cover 17 are chosen to be optically transparent if required.

The following embodiments of a cartridge 1 and a system 40 and combinations thereof are also preferred:

A cartridge 1, wherein the flexibly deformable top structure 7 is configured as a flexible foil that is sealingly attached to the upper surface 3 of a plate-like structure 2' or frame structure 2".

A cartridge 1, wherein a piercable bottom structure 8 is configured as a piercable bottom portion of a body 2 that is integrated in a plate-like structure 2' or frame structure 2".

A cartridge 1, wherein a piercable bottom structure 8 is configured as a piercable foil that is sealingly attached to a lower surface 4 of a plate-like structure 2' or frame structure 2".

A cartridge 1, which comprises intermediate spacers 15 that are located within an area of a gap 12 and that are integrally formed with a plate-like structure 2' or frame structure 2".

A cartridge 1, wherein piercing elements 13 are located within an area of a gap 12 and close to a peripheral rim 9', the piercing elements 13 being attached to a peripheral rim 9' and/or to a lower surface 4 of a body 2 of a plate-like structure 2' or frame structure 2".

A cartridge 1, which comprises intermediate spacers 15 configured as separate elements located within an area of a gap 12 and attached to a lower surface 4 of a body 2 of a plate-like structure 2' or frame structure 2".

A cartridge 1, wherein piercing elements 13 are located within an area of a gap 12 and are integrally formed with a separate ring-like element 9" that surrounds the gap 12.

A cartridge 1, wherein a central opening 14 of a frame structure 2" is configured as a depression in an upper surface 3 leaving a bottom portion 16 of a body 2 that is integrally formed with the frame structure 2" to form a substantially flat lower surface 4 of the body 2.

A cartridge 1, which comprises a rigid cover 17 attached to a frame structure 2", the rigid cover 17 closing a gap 12 on a side opposite to a working film 10, a lower surface of the rigid cover 17 being essentially flush with a lower surface 4 of the frame structure 2".

A cartridge 1, wherein a rigid cover 17 has essentially the same extension as a frame structure 2" and comprises a number of holes 18 located below wells 5, the holes 18 having a size and shape sufficient to allow bended piercing elements 13 to abut and pierce a respective piercable bottom structure 8 of a well 5.

A cartridge 1, wherein a cover layer 19 is configured as a piercable foil that is sealingly attached to a lower surface 4 of a frame structure 2" or of a plate-like structure 2'.

A cartridge 1, wherein a cover layer 19 is electrically conductive and is hydrophobic at least on a surface directed to a gap 12, the cartridge 1 comprising an electrical ground connection 54 that is connected to a cover layer 19 and that is attachable to a ground potential source.

A cartridge 1, wherein an intake device 26 comprises:
a) a cylinder tube 27 with a first end 28 and with a second end 29,
b) a plunger 30 that is insertable on a first tube end 28 and that is movable in the cylinder tube 27, and
c) a sealing foil 31 that sealingly closes the second end 29 of the cylinder tube 27.

A system 40, which comprises actuating elements 41 for actuating piercing elements 13 of a cartridge 1, the piercing elements 13 being configured for piercing at least a piercable bottom structure 8 of the cartridge 1 and thus for releasing reagents, treatment liquids, reaction liquids or sample containing liquids into a gap 12 of the cartridge 1.

A system 40, which comprises actuating elements 41 for actuating flexibly deformable top structures 7 of a cartridge 1, the flexibly deformable top structures 7 being configured to be pushed inwards by an actuating element 41 and to thereby reduce the internal volume of an inner chamber of an intake recess 25 or an internal volume of a well 5 for releasing lysate, reagents, treatment liquids, or reaction liquids to a gap 12 of the cartridge 1.

A system 40, wherein actuating elements 41 are configured as plungers that are slidingly movable in guiding channels 45 and that are agitated by an agitation mechanism 46.

A system 40, wherein an agitation mechanism 46 for agitating actuating elements 41 is configured as one of a wax pump bladder, a solenoid driven or clamping mechanism driven lever 51.

A system 40, wherein an agitation mechanism 46 for agitating actuating elements 41 is configured as a clamping mechanism driven lever 51, a clamping mechanism 52 being hand driven and configured to press a body 2,2',2" of a cartridge 1 onto a substrate 42 and electrode array 20 of the system 40.

A system 40, wherein a substrate 42 comprises an abutment surface 47 which is offset to a surface level 48 of electrodes 44 such that a peripheral rim 9' or separate peripheral element 9" of a cartridge 1 to which a working film 10 is attached is movable beyond the surface level 48 of the electrodes 44 for stretching the working film 10 on the electrodes 44.

A system 40, wherein a substrate 42 comprises a surface 49 which is offset to a surface level 48 of electrodes 44 such that at least a part of a lower surface 4 of a body 2,2',2" or of a spacer 9 of a cartridge 1 to which a working film 10 is attached is movable beyond the surface level 48 of the electrodes 44 for stretching the working film 10 on the electrodes 44.

A system 40, wherein a substrate 42 comprises an electrically insulating film, layer or cover 50 that is applied to an electrode array 20, that covers all individual electrodes 44 of the electrode array 20 and that separates the individual electrodes 44 from each other.

| Reference numbers | |
|---|---|
| 1 | cartridge |
| 2, 2', 2" | body |
| 2' | plate-like structure of 2 |
| 2" | frame structure of 2 |
| 3 | upper surface of 2, 2', 2" |
| 4 | lower surface of 2, 2', 2" |
| 5 | well |
| 6 | reagent |
| 6' | sample |
| 7 | flexibly deformable top structure |
| 8 | piercable bottom structure |
| 9 | peripheral spacer |
| 9' | integrated peripheral rim |
| 9" | separate peripheral element |
| 10 | working film |
| 11 | hydrophobic upper surface of 10 |
| 12 | gap |
| 13 | piercing element |
| 14 | central opening |
| 15 | intermediate spacer |
| 16 | bottom portion |
| 17 | rigid cover |
| 18 | cover hole |
| 19 | cover layer |
| 20 | electrode array |
| 21 | optical fiber |
| 22 | window |
| 23 | droplet |
| 24 | specimen intake |
| 25 | intake recess |
| 25' | alternative intake recess |
| 26 | intake device |
| 27 | cylinder tube |
| 28 | first end of 27 |
| 29 | second end of 27 |
| 30 | plunger |
| 31 | sealing foil |
| 40 | system with 20 |
| 41 | actuating element |
| 42 | substrate |
| 43 | central control unit |
| 44 | individual electrode |
| 45 | guiding channel |
| 46 | agitation mechanism |
| 47 | abutment surface |
| 48 | surface level of 44 |
| 49 | surface of 42 |
| 50 | electrically insulating film, layer or cover |
| 51 | lever |
| 52 | clamping mechanism |
| 53 | outer part of 2 |
| 54 | ground connection |
| 55 | buccal swab head |
| 56 | frit |
| 57 | downward extension of 2 |
| 58 | seal |
| 59 | piercing structure |
| 60 | optically transparent electrode |
| 61 | optical via electrode |
| 62 | through hole in 61 |
| 63 | flanking electrode |
| 64 | electrode selection unit |

What is claimed is:

1. A system (40) for liquid droplet manipulation, the liquid droplet manipulation system (40) comprising:
   i) a substrate (42) with at least one electrode array (20) and
   ii) a central control unit (43) configured to control the selection of individual electrodes (44) of said at least one electrode array (20) and for providing the electrodes (44) with individual voltage pulses for manipulating liquid droplets (23) by electrowetting,
   wherein the liquid droplet manipulation system (40) is configured to receive on top of the electrodes (44) a working film (10) for manipulating samples in liquid droplets (23) with the electrode array(s) (20) when the working film (10) is placed on said at least one electrode array (20),
   wherein the liquid droplet manipulation system (40) further comprises:
   iii) at least one disposable cartridge (1) that is removably placed on said at least one electrode array (20) of the liquid droplet manipulation system (40),
   wherein the at least one disposable cartridge (1) comprises:
   a) a body (2,2',2") that comprises an upper surface (3), a lower surface (4), and a number of wells (5) configured to hold therein reagents (6) or samples (6');
   b) a flexibly deformable top structure (7) impermeable to liquids and configured to seal a top side of the wells (5);
   c) a piercable bottom structure (8) impermeable to liquids and configured to seal a bottom side of the wells (5);
   d) a working film (10) located below the lower surface (4) of the body (2,2',2"), the working film (10) being impermeable to liquids and comprising a hydrophobic upper surface (11);
   e) a peripheral spacer (9,9',9") located below the lower surface (4) of the body (2,2',2") and connecting the working film (10) to the body (2,2',21");
   f) a gap (12) between the lower surface (4) of the body (2,2',2") and the hydrophobic upper surface (11) of the working film (10), the gap (12) being defined by the peripheral spacer (9,9',9"); and
   g) a number of piercing elements (13) located below piercable bottom structures (8) and configured to pierce the piercable bottom structures (8) for releasing reagents or samples (6,6') from the wells (5) into the gap (12),
   wherein at least one selected individual electrode (44) of said at least one electrode array (20) of the liquid droplet manipulation system (40) is configured to be penetrated by light of an optical detection system for the optical inspection or analysis of samples in liquid droplets (23) that are located on the working film (10) of the disposable cartridge, and
   wherein the at least one selected individual electrode (44) is configured as an optical via electrode (61) that comprises a through hole (62).

2. The liquid droplet manipulation system (40) of claim 1, wherein the working film (10) of the cartridge (1) is configured as a monolayer of electrically non-conductive material, the upper surface (11) of the working film (10) being treated to be hydrophobic.

3. The liquid droplet manipulation system (40) of claim 1, wherein the optical via electrode (61) is located in place of an individual electrode (44) in an electrode path (65) or within a grid-like electrode array (66) and is configured to be addressed by an electrode selection unit (64) of the central control unit (43).

4. The liquid droplet manipulation system (40) of claim 1, wherein the substrate (42) comprises at least one optical fiber (21) for bringing light to a through hole (62) of an optical via electrode (61) and thus to a droplet (23) on the working film (10) that is placed on said electrode array (20).

5. The liquid droplet manipulation system (40) of claim 4, wherein the at least one optical fiber (21) belongs to an optical bottom reading system and a detector connected to the latter, the optical bottom reading system being configured to send excitation light to the sample and to receive and detect fluorescence emitted by a sample in a liquid droplet (23) that is located on the working film (10).

6. The liquid droplet manipulation system (40) of claim 4, wherein the optical fiber (21) is integrated into the substrate (42) of the electrode array (20) of the system (40) for the manipulation of droplets.

7. The liquid droplet manipulation system (40) of claim 1, wherein the substrate (42) comprises electrical lines that link the individual electrodes (44) with an electrode selection unit (64) of the central control unit (43) of the liquid droplet manipulation system (40).

8. The liquid droplet manipulation system (40) of claim 7, wherein the optical fiber (21) is integrated into the substrate (42) of the electrode array (20) of the system (40) for the manipulation of droplets.

9. The liquid droplet manipulation system (40) of claim 1, wherein the working film (10) is optically transparent and configured as a monolayer of a hydrophobic material.

10. The liquid droplet manipulation system (40) of claim 1, wherein the working film (10) is optically transparent and configured as a laminate of a hydrophobic upper layer and a dielectric lower layer.

11. A system (40) for liquid droplet manipulation, the liquid droplet manipulation system (40) comprising:
a) a substrate (42) with at least one electrode array (20) and
b) a central control unit (43) configured to control the selection of individual electrodes (44) of said at least one electrode array (20) and for providing the electrodes (44) with individual voltage pulses for manipulating liquid droplets (23) by electrowetting,
wherein the liquid droplet manipulation system (40) is configured to receive on top of the electrodes (44) a working film (10) for manipulating samples in liquid droplets (23) with the electrode array(s) (20) when the working film (10) is placed on said at least one electrode array (20),
wherein the liquid droplet manipulation system (40) further comprises:
c) a working film (10) for manipulating samples in liquid droplets (23) with said at least one electrode array (20), the working film (10) being placed on said at least one electrode array (20) and being comprised by a disposable cartridge (1) that is removably placed on said at least one electrode array (20) of the liquid droplet manipulation system (40),
wherein at least one selected individual electrode (44) of said at least one electrode array (20) of the liquid droplet manipulation system (40) is configured to be penetrated by light of an optical detection system for the optical inspection or analysis of samples in liquid droplets (23) that are located on the working film (10) of the disposable cartridge,
wherein the at least one selected individual electrode (44) is configured as an optical via electrode (61) that comprises a through hole (62)
wherein said optical via electrode (61) has a first area and the through hole (62) of said optical via electrode (61) has a second area, and
wherein an area ratio (optical via electrode (61):through hole (62)) is from 1.8 to 2.8.

12. The liquid droplet manipulation system (40) of claim 11, wherein the area ratio (optical via electrode (61):through hole (62)) is 2.4.

13. The liquid droplet manipulation system (40) of claim 11, wherein the optical via electrode (61) is divided into two partial electrodes, each of which comprising a part of the through hole (62).

14. The liquid droplet manipulation system (40) of claim 13, wherein the two partial electrodes are individually connected to the electrode selection unit (64) so that they can be individually activated or deactivated.

15. The liquid droplet manipulation system (40) of claim 11, wherein the substrate (42) comprises at least one optical fiber (21) for bringing light to a through hole (62) of an optical via electrode (61) and thus to a droplet (23) on the working film (10) that is placed on said electrode array (20).

16. The liquid droplet manipulation system (40) of claim 11, wherein the substrate (42) comprises electrical lines that link the individual electrodes (44) with an electrode selection unit (64) of the central control unit (43) of the liquid droplet manipulation system (40).

17. The liquid droplet manipulation system (40) of claim 15, wherein the at least one optical fiber (21) belongs to an optical bottom reading system and a detector connected to the latter, the optical bottom reading system being configured to send excitation light to the sample and to receive and detect fluorescence emitted by a sample in a liquid droplet (23) that is located on the working film (10).

18. The liquid droplet manipulation system (40) of claim 15, wherein the optical fiber (21) is integrated into the substrate (42) of the electrode array (20) of the system (40) for the manipulation of droplets.

19. The liquid droplet manipulation system (40) of claim 16, wherein the optical fiber (21) is integrated into the substrate (42) of the electrode array (20) of the system (40) for the manipulation of droplets.

20. The liquid droplet manipulation system (40) of claim 11, wherein the working film (10) is optically transparent and configured as a monolayer of a hydrophobic material.

21. The liquid droplet manipulation system (40) of claim 11, wherein the working film (10) is optically transparent and configured as a laminate of a hydrophobic upper layer and a dielectric lower layer.

22. The liquid droplet manipulation system (40) of claim 11, wherein the optical via electrode (61) is located in place of an individual electrode (44) in an electrode path (65) or within a grid-like electrode array (66) and is configured to be addressed by an electrode selection unit (64) of the central control unit (43).

* * * * *